(12) United States Patent
Ohi et al.

(10) Patent No.: US 12,220,410 B2
(45) Date of Patent: Feb. 11, 2025

(54) ANTITUMOR COMPOSITION

(71) Applicant: OTSUKA PHARMACEUTICAL CO., LTD., Tokyo (JP)

(72) Inventors: Naoto Ohi, Osaka (JP); Mitsuhiro Okuno, Osaka (JP); Hideo Tanaka, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 708 days.

(21) Appl. No.: 17/429,531

(22) PCT Filed: Mar. 25, 2020

(86) PCT No.: PCT/JP2020/013454
§ 371 (c)(1),
(2) Date: Aug. 9, 2021

(87) PCT Pub. No.: WO2020/196665
PCT Pub. Date: Oct. 1, 2020

(65) Prior Publication Data
US 2022/0202794 A1 Jun. 30, 2022

(30) Foreign Application Priority Data
Mar. 25, 2019 (JP) .................... 2019-057029

(51) Int. Cl.
*A61K 31/4412* (2006.01)
*A61K 45/06* (2006.01)
*A61P 35/00* (2006.01)

(52) U.S. Cl.
CPC .......... *A61K 31/4412* (2013.01); *A61K 45/06* (2013.01); *A61P 35/00* (2018.01)

(58) Field of Classification Search
CPC ............................ A61K 31/4412; A61P 35/00
USPC ........................................................ 514/349
See application file for complete search history.

(56) References Cited

U.S. PATENT DOCUMENTS 8,946,437 B2 * 2/2015 Nakagawa ............ C07D 213/76
546/290

FOREIGN PATENT DOCUMENTS

RU 2 632 915 C2 10/2017
WO 2012/046825 A1 4/2012

OTHER PUBLICATIONS

CDC, Picture of America Prevention, https://www.cdc.gov/pictureofamerica/pdfs/picture_of_america_prevention.pdf, accessed Dec. 8, 2023, first published Jul. 2, 2017 (Year: 2017).*
CDC, Picture of America Prevention, https://www.cdc.gov/pictureofamerica/pdfs/picture_of_america_prevention.pdf, accessed Dec. 8, 2023, first published Jul. 2, 2017, Wayback Machine (Year: 2017).*
Lollini et al., Published Oct. 2002, Cancer Immunology, Immunotherapy, vol. 51, pp. 409-416 (Year: 2002).*
Noel J.-M. Raynal et al., "Repositioning FDA-Approved Drugs in Combination with Epigenetic Drugs to Reprogram Colon Cancer Epigenome", Molecular Cancer Therapy, 2017, vol. 16, No. 2, pp. 397-407 (27 pages total).
Preobrazhenskaya, M. N., "Developments in the Research of New Antitumor Agents* (Review)," Chemistry of Heterocyclic Compounds, Jan. 1985, vol. 21, No. 1, pp. 13-24 (12 pages total).
Indian Office Action issued Jun. 7, 2023 in Indian Application No. 202117038456.
Enrique Espinosa, et al. "Classification of anticancer drugs—a new system based on therapeutic targets", Cancer Treatment Reviews, vol. 29, No. 6, Nov. 30, 2003, pp. 515-523.
Ahmet Can Timucin, et al., "Selective targeting of antiapoptotic BCL-2 proteins In cancer", Medicinal Research Reviews, vol. 39, No. 1, Jan. 1, 2019, pp. 146-175.
Takahiro Sato, et al., "DNA Hypomethylating Drugs in Cancer Therapy", Cold Spring Harbor Perspectives in Medicine, vol. 7, No. 5, Feb. 3, 2017, p. a026948 (15 pages).
International Search Report for PCT/JP2020/013454 dated Jul. 6, 2020 (PCT/ISA/210).
Written Opinion for PCT/JP2020/013454 dated Jul. 6, 2020 (PCT/ISA/237).

(Continued)

*Primary Examiner* — Yih-Horng Shiao
*Assistant Examiner* — Jaret J Crews
(74) *Attorney, Agent, or Firm* — Sughrue Mion, PLLC

(57) ABSTRACT

A combination of antitumor agents significantly shrinks tumors by synergistic antitumor action without increasing side effects to the extent possible. The antitumor composition contains compound (B) or a salt thereof for use in combination with antitumor agent (A), where (A) is at least one antitumor agent selected from alkylating agents, CD20 recognition molecules, DNA methylation inhibitors, pyrimidine antimetabolites, purine antimetabolites, antifolates, Bcl-2 inhibitors, and tyrosine kinase inhibitors; and (B) is a compound or a salt thereof represented by formula (1):

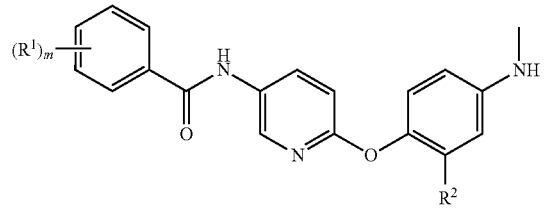

(1)

where $R^1$ is halogen, aryl, aryloxy, or lower alkyl optionally substituted with one or more halogen atoms; $R^2$ is hydrogen, halogen, lower alkyl, or lower alkoxy; and m=1 to 3, provided that when m is 2 or 3, each $R^1$ is the same or different.

7 Claims, 24 Drawing Sheets

(56) References Cited

OTHER PUBLICATIONS

Ting-Chao Chou, "Drug Combination Studies and Their Synergy Quantification Using the Chou-Talalay Method", Cancer Res, Jan. 15, 2010, vol. 70, No. 2, pp. 440-446 (7 pages total).
Office Action issued Oct. 25, 2023 in Eurasian Application No. 202192598.

\* cited by examiner

[Fig. 1]
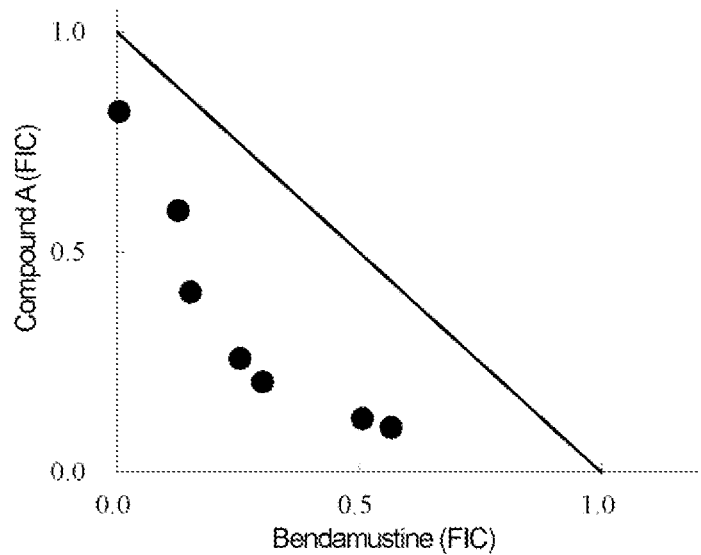
[Fig. 2]
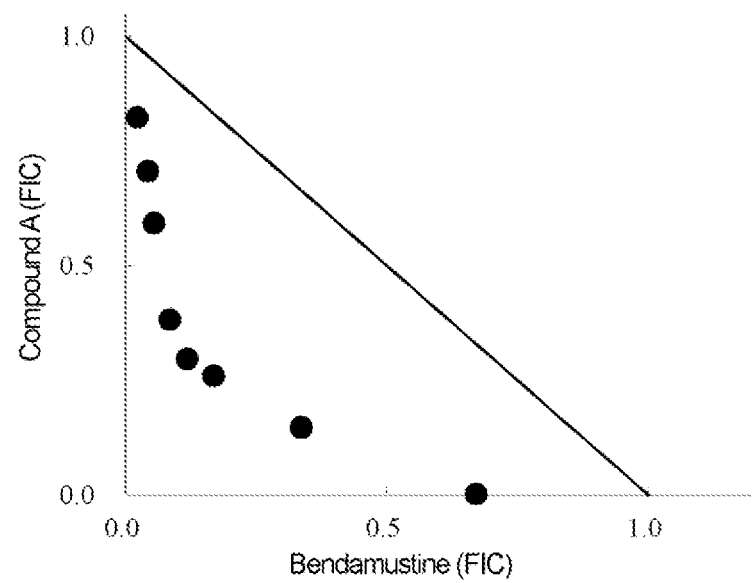

[Fig. 3]
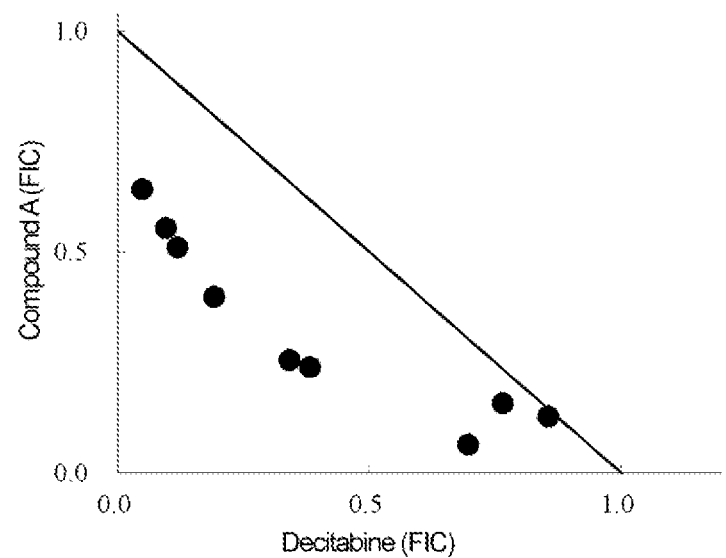
[Fig. 4]
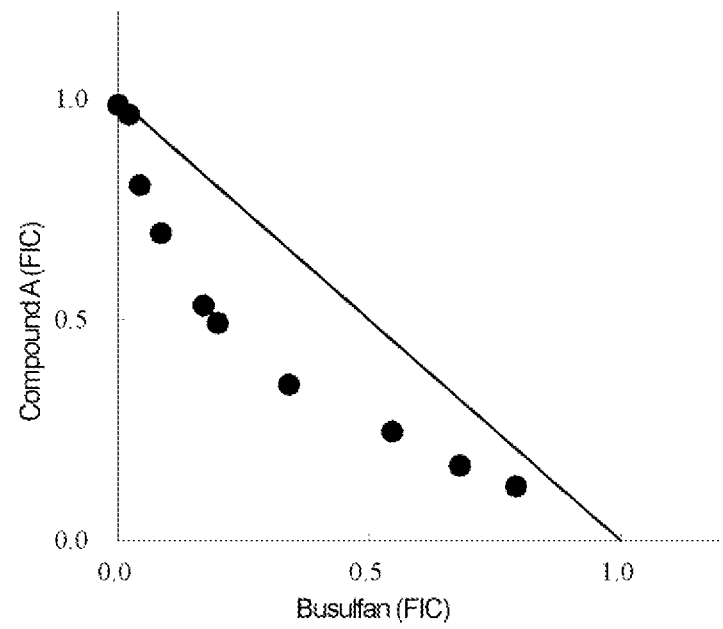

[Fig. 5]
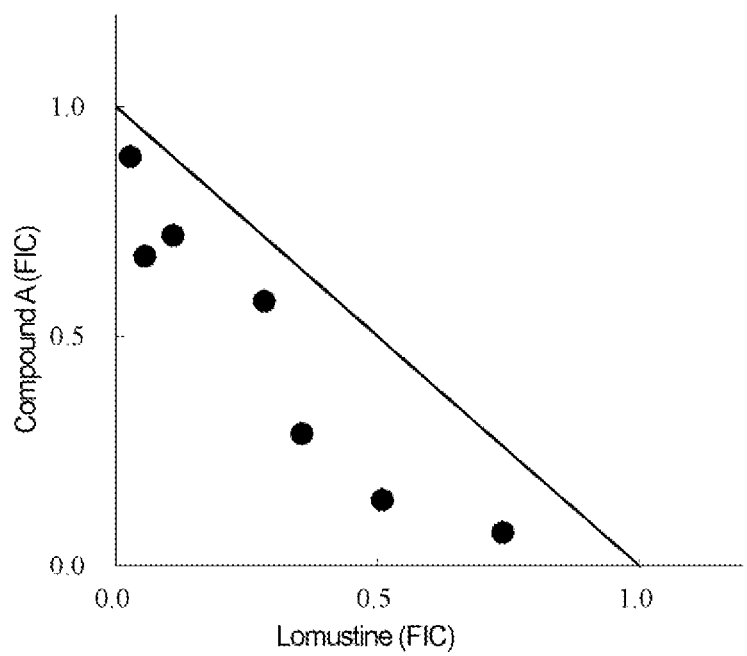
[Fig. 6]
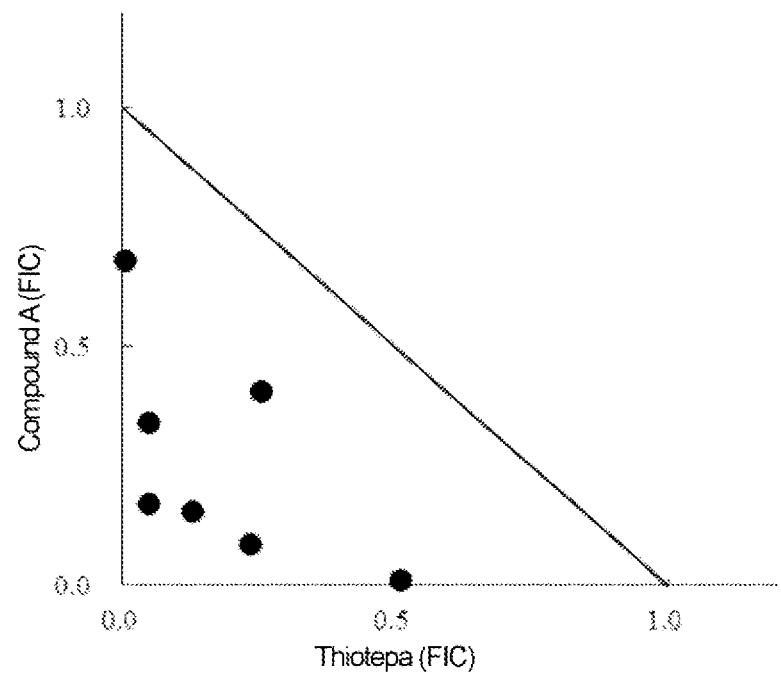

[Fig. 7]
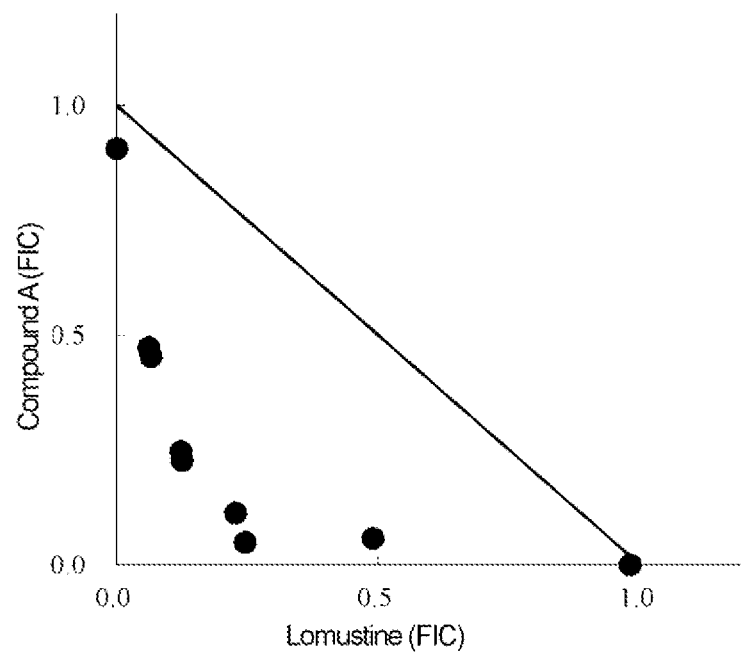
[Fig. 8]
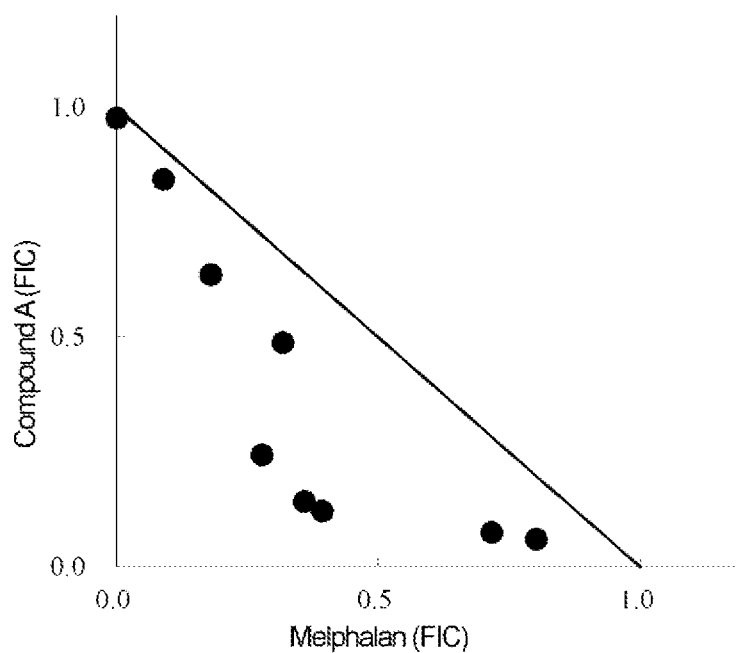

[Fig. 9]
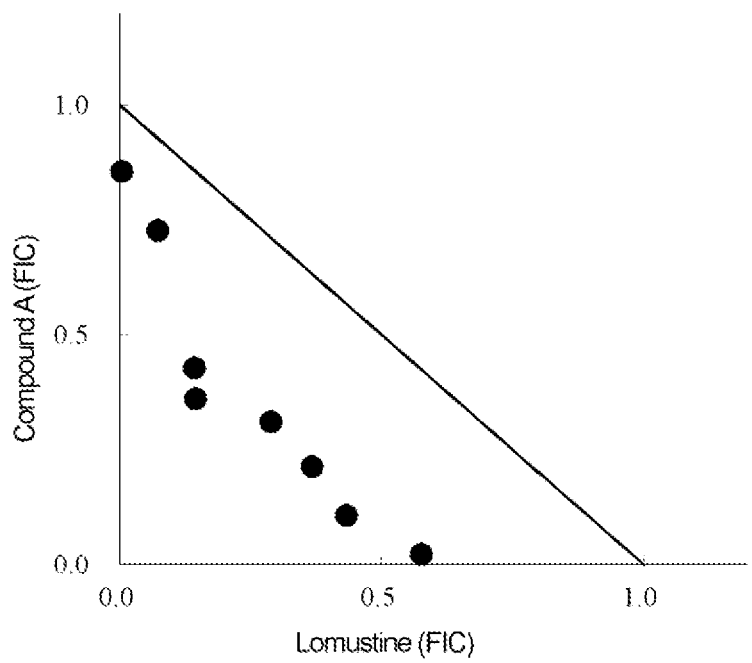
[Fig. 10]
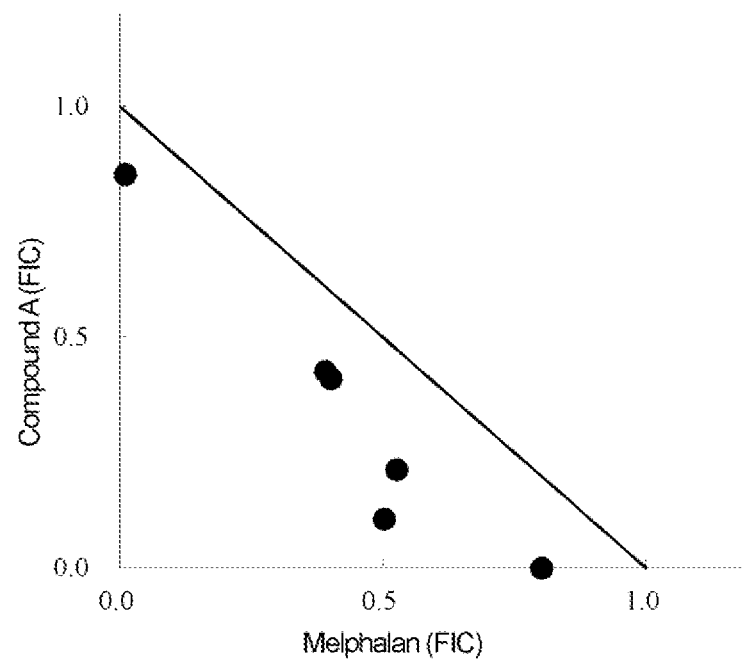

[Fig. 11]
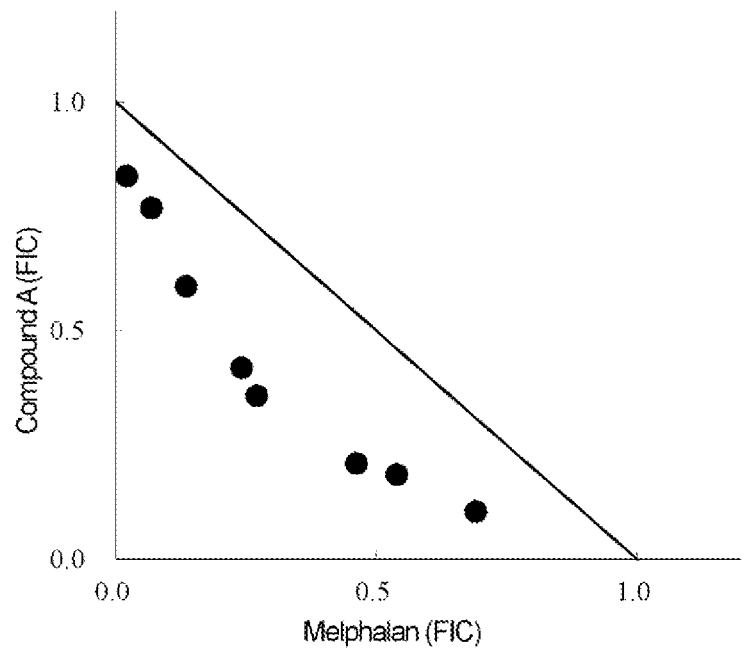
[Fig. 12]
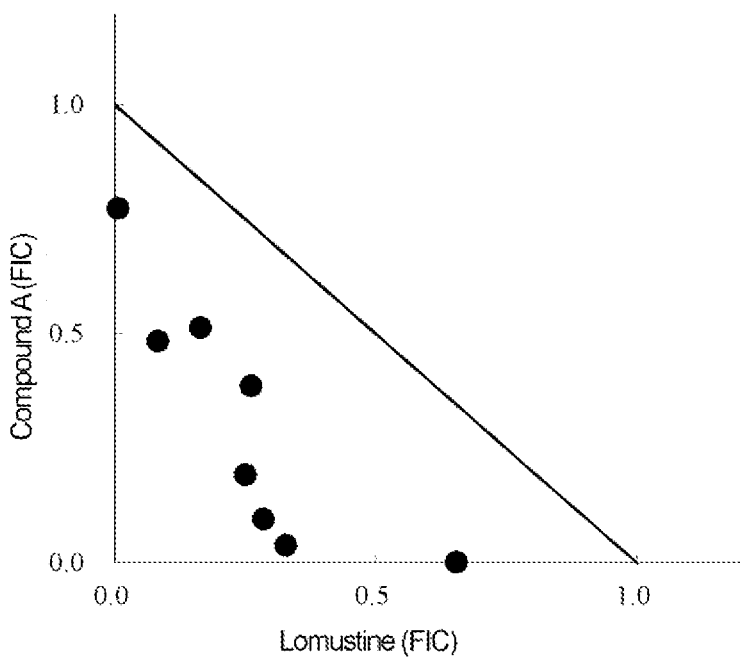

[Fig. 13]
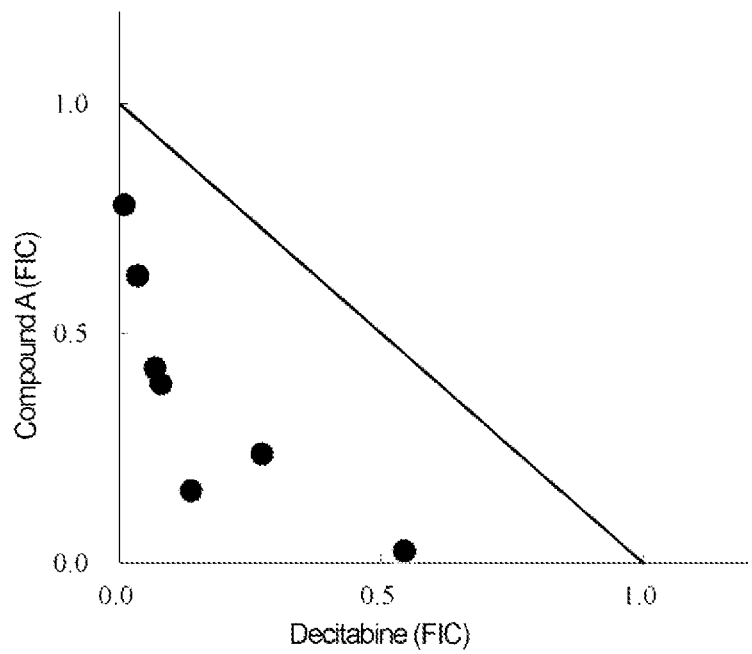
[Fig. 14]
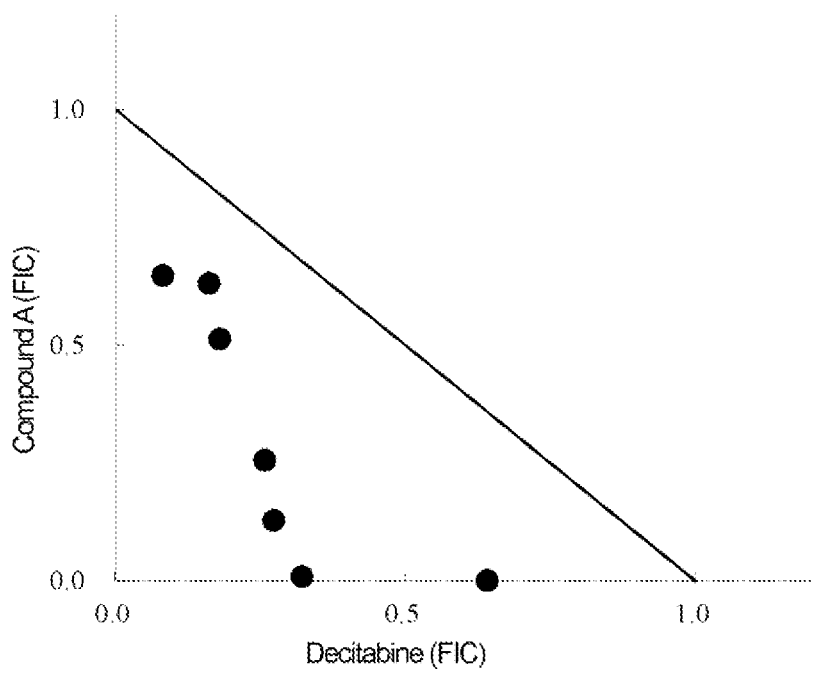

[Fig. 15]
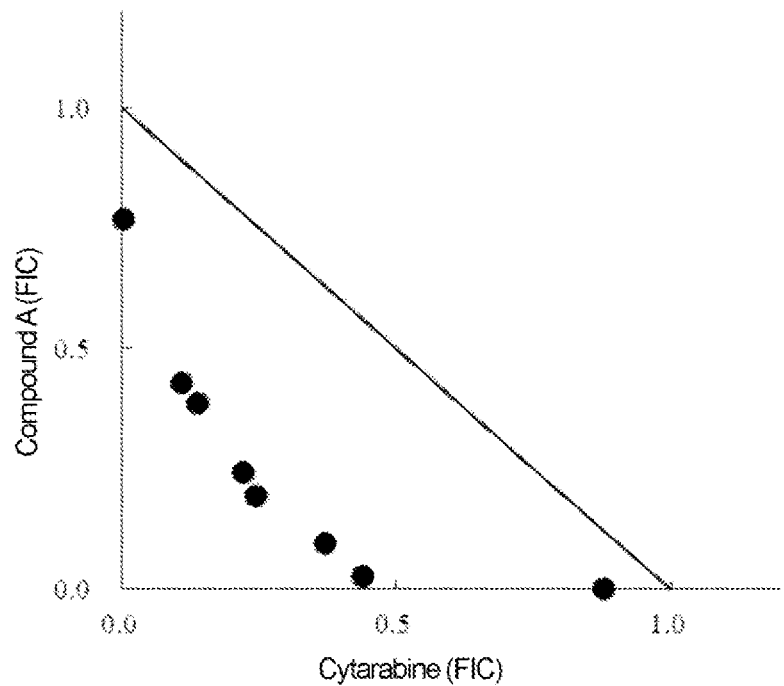
[Fig. 16]
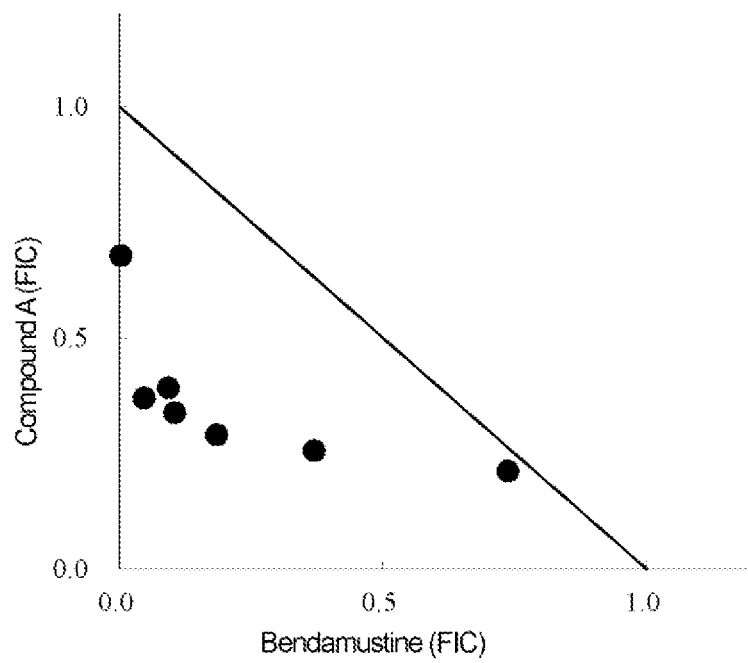

[Fig. 17]
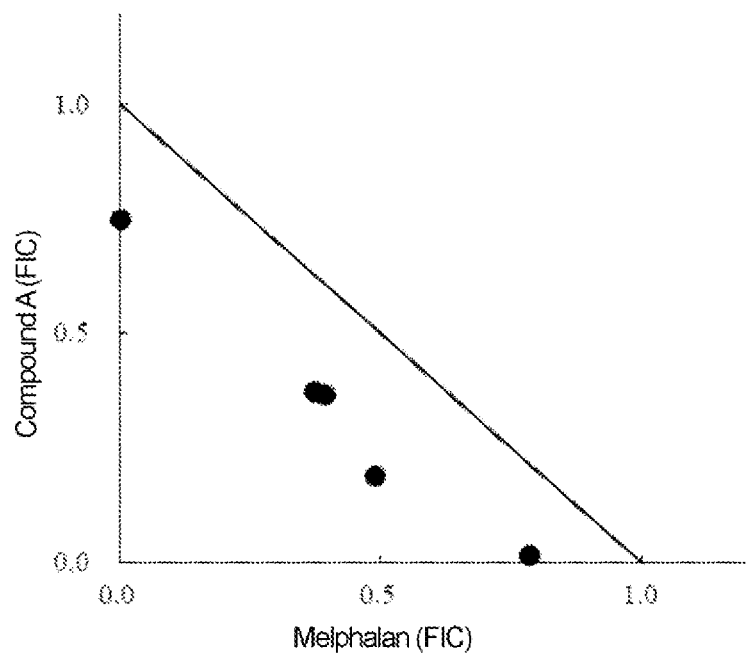
[Fig. 18]
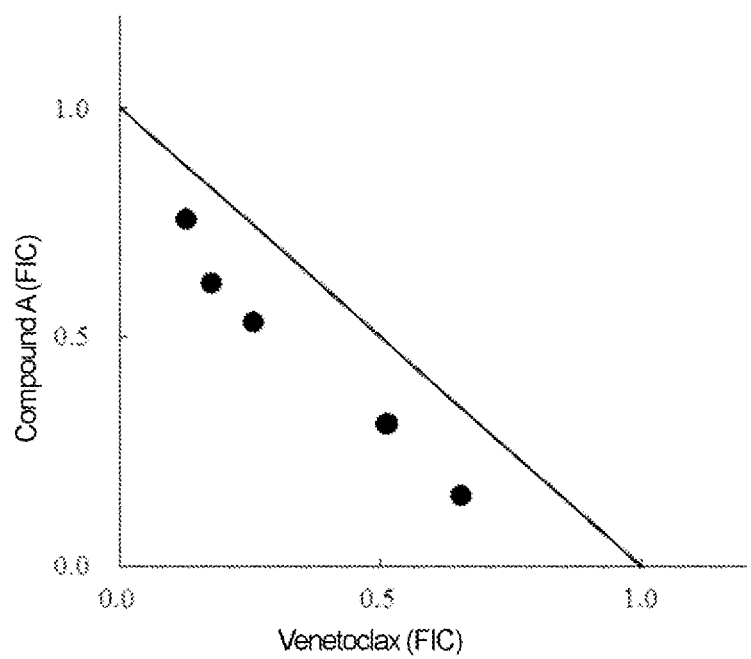

[Fig. 19]
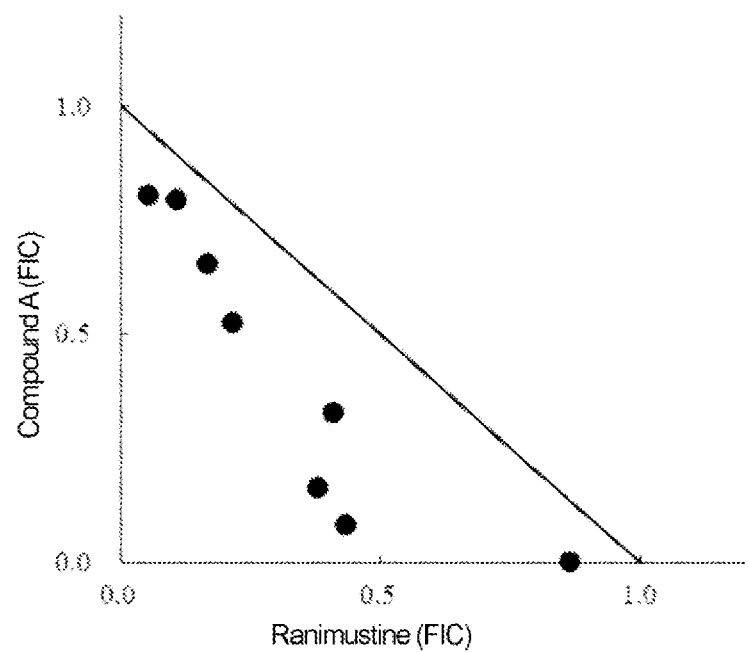
[Fig. 20]
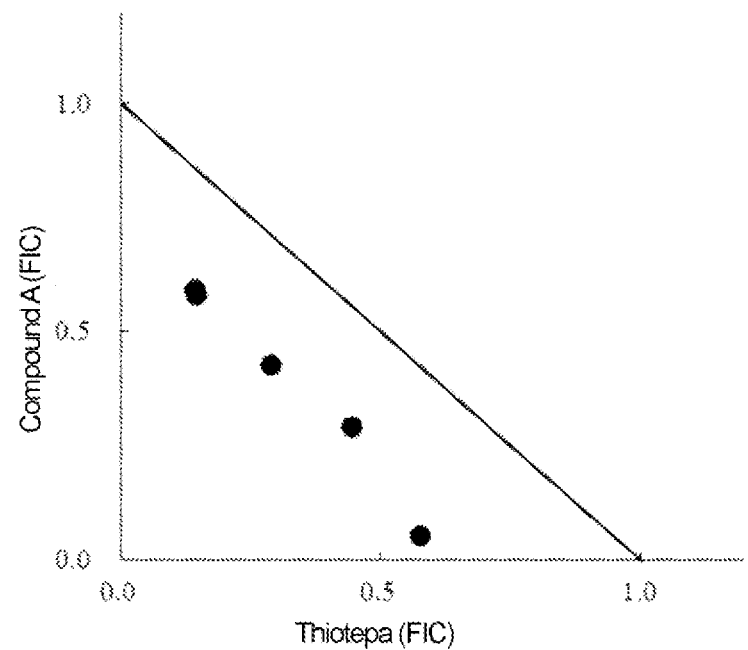

[Fig. 21]
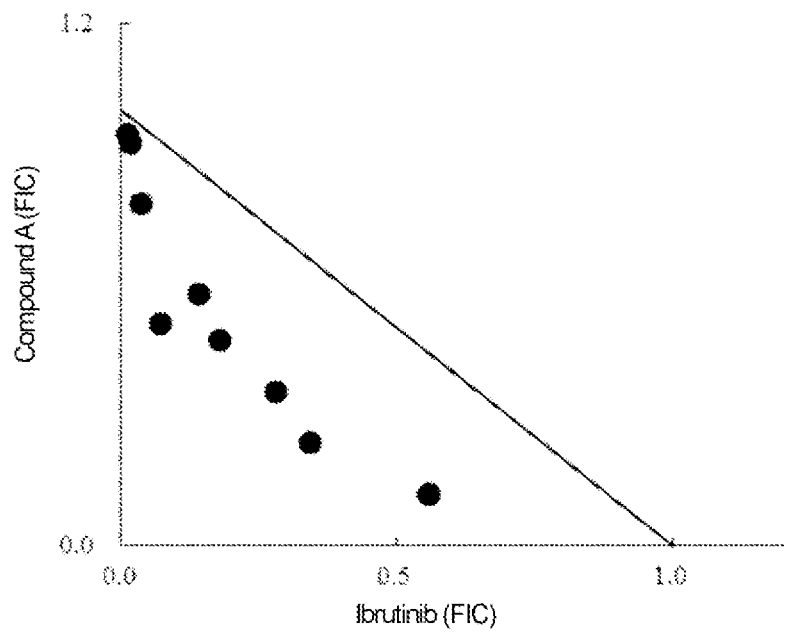
[Fig. 22]
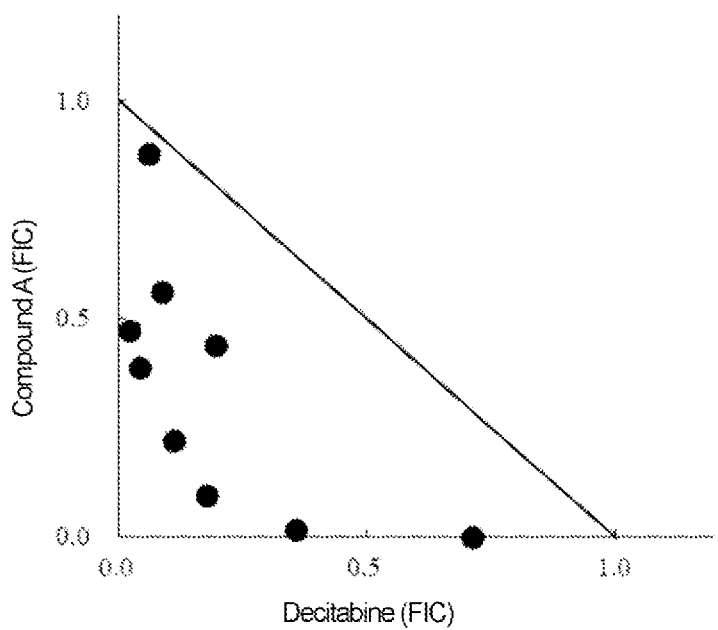

[Fig. 23]
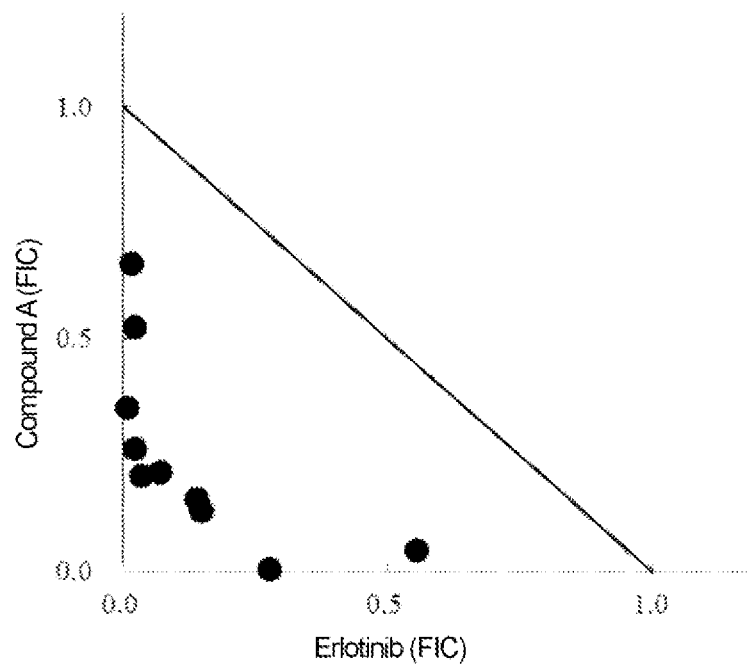
[Fig. 24]
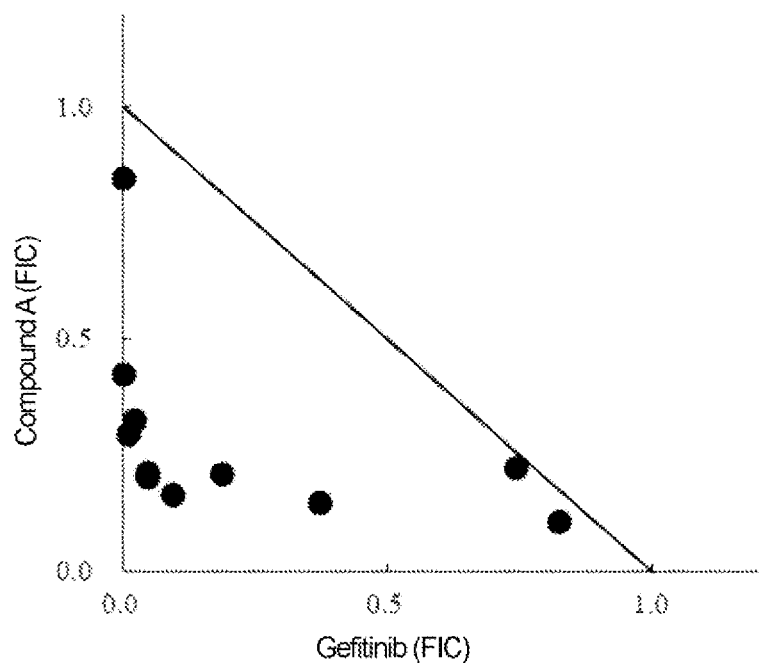

[Fig. 25]
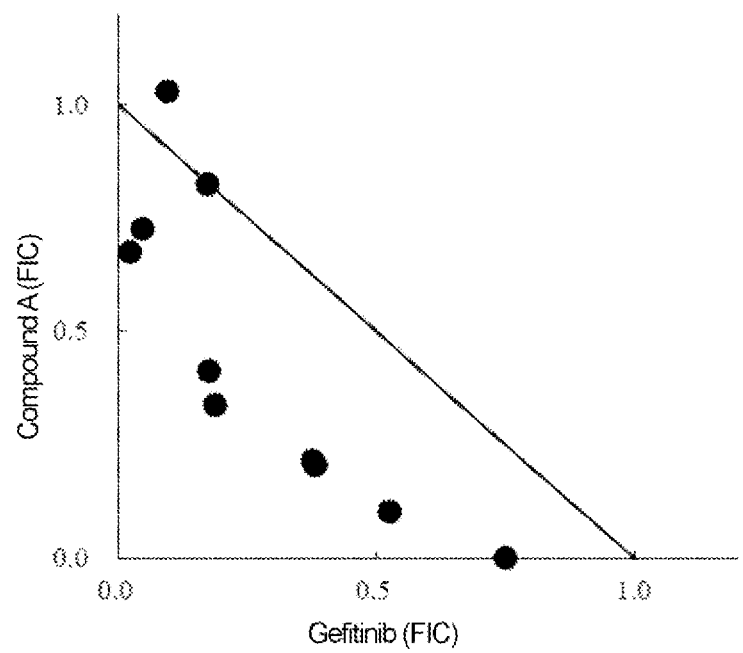
[Fig. 26]
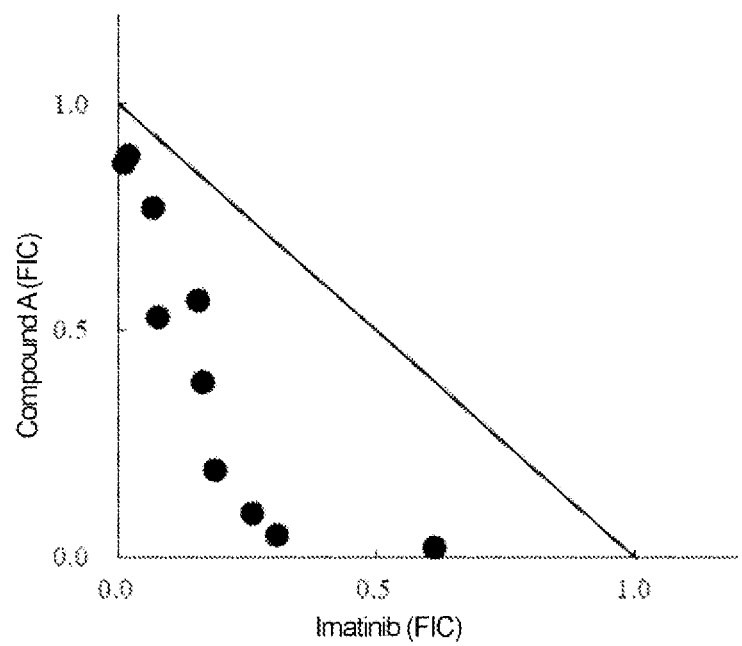

[Fig. 27]
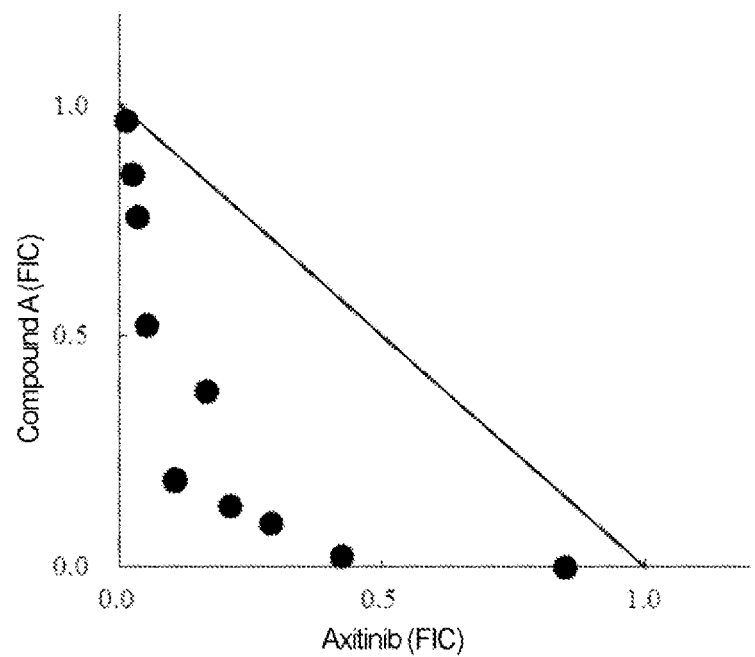
[Fig. 28]
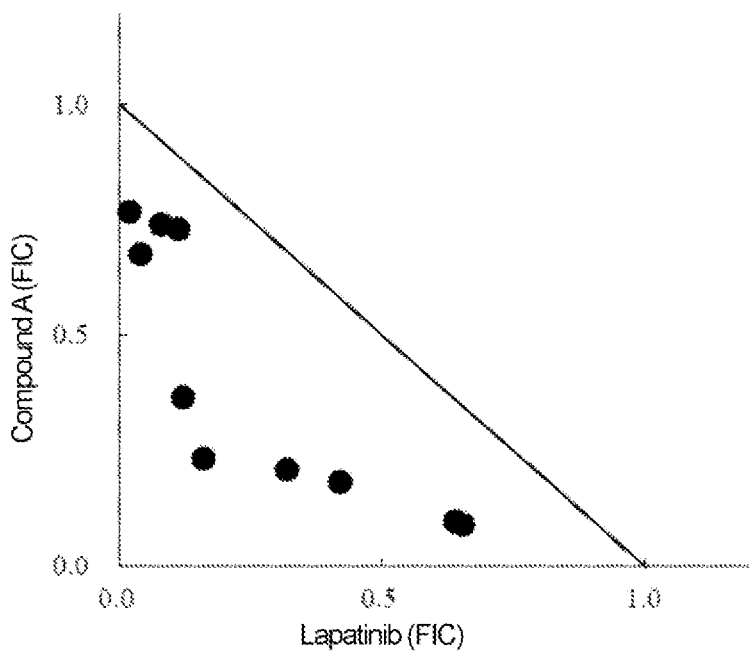

[Fig. 29]
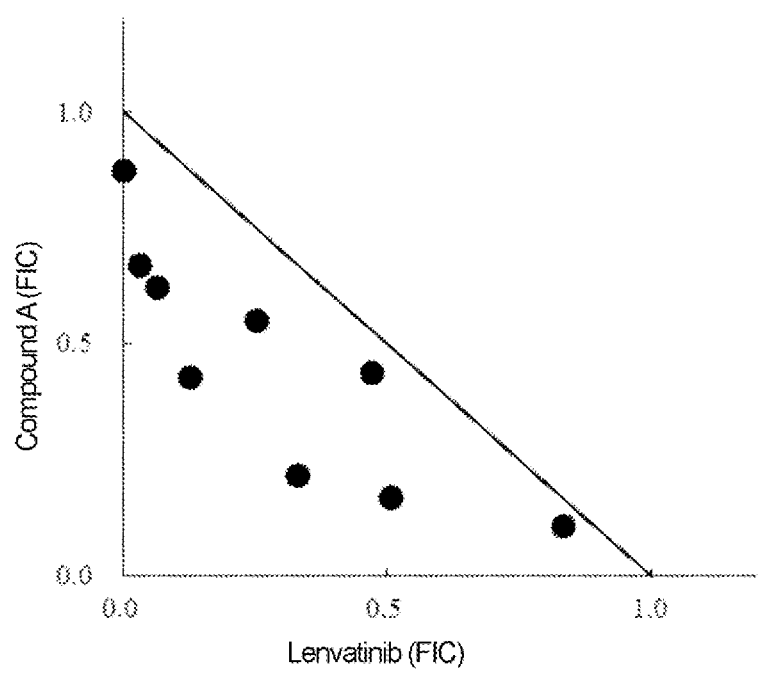
[Fig. 30]
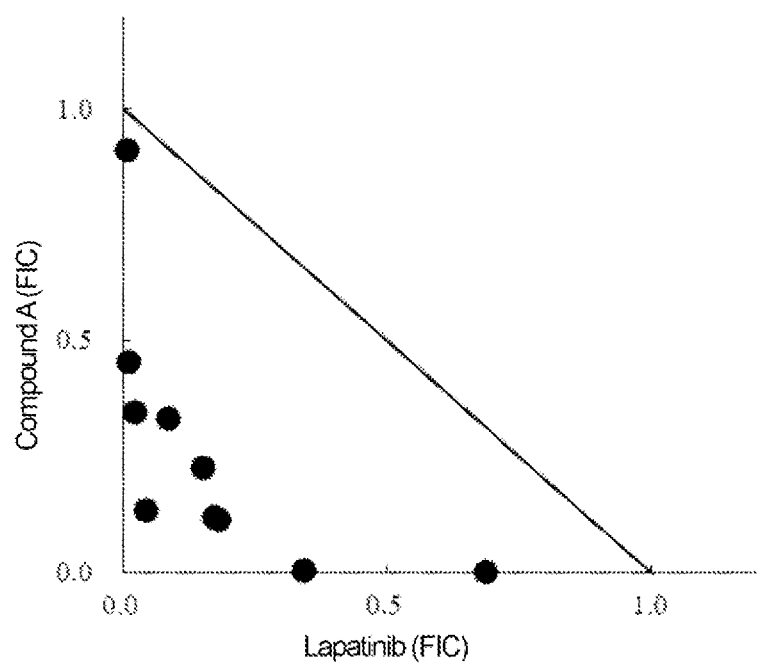

[Fig. 31]
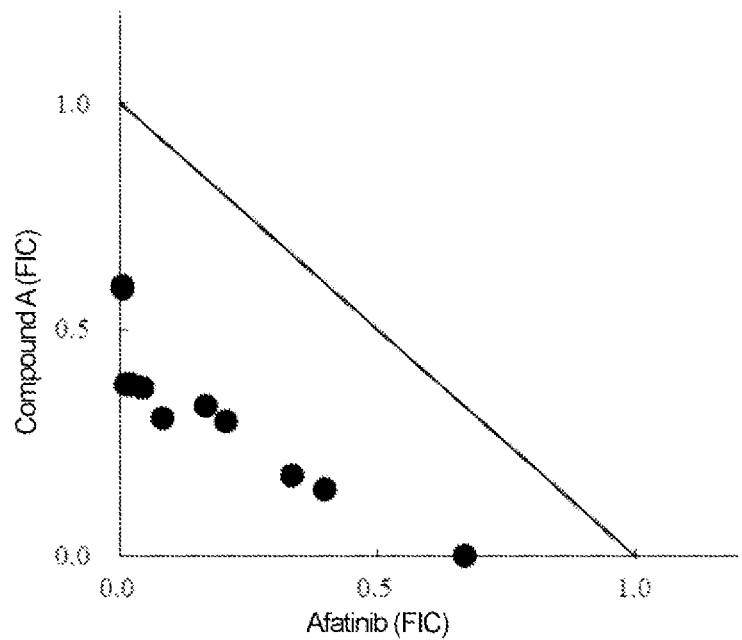
[Fig. 32]
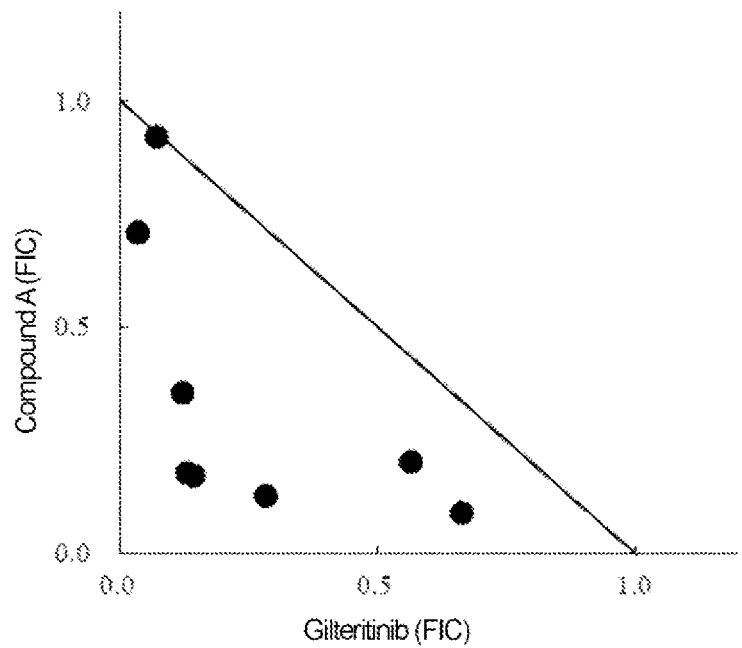

[Fig. 33]
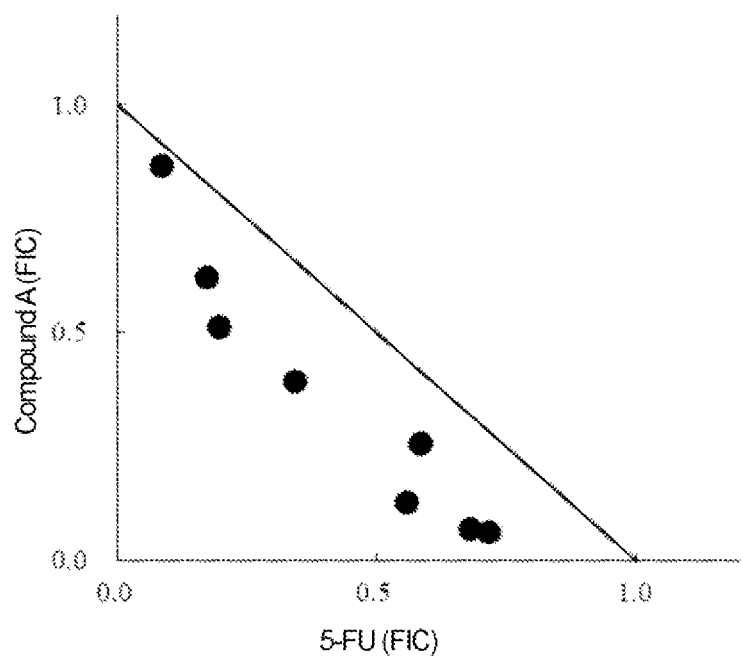
[Fig. 34]
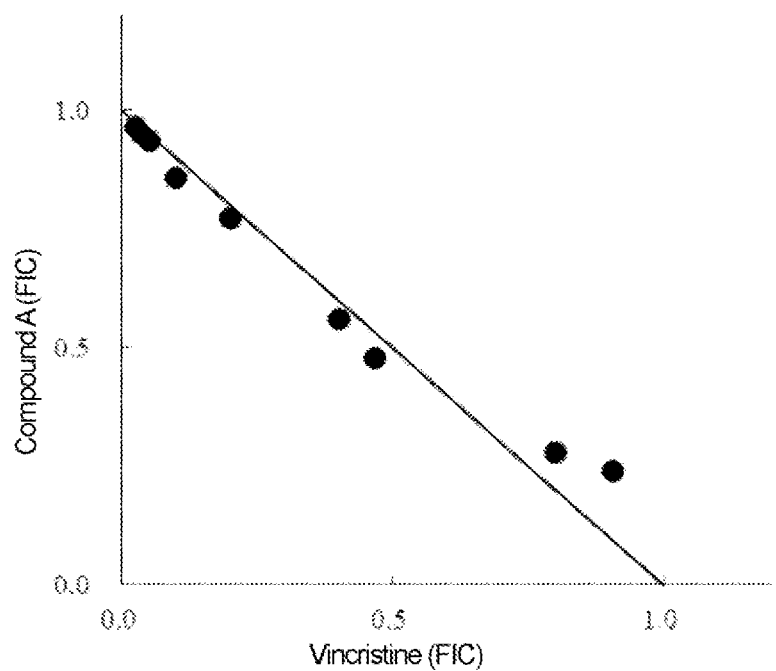

[Fig. 35]
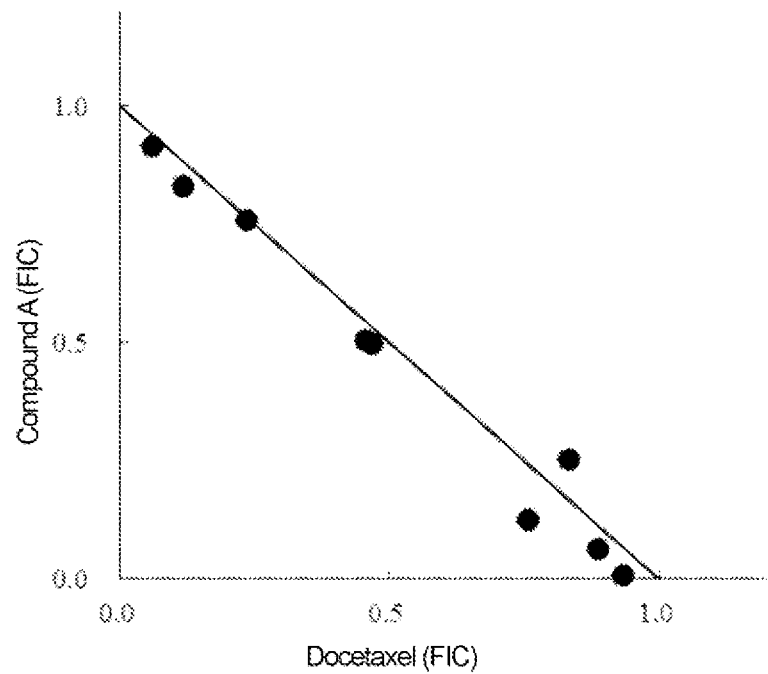
[Fig. 36]
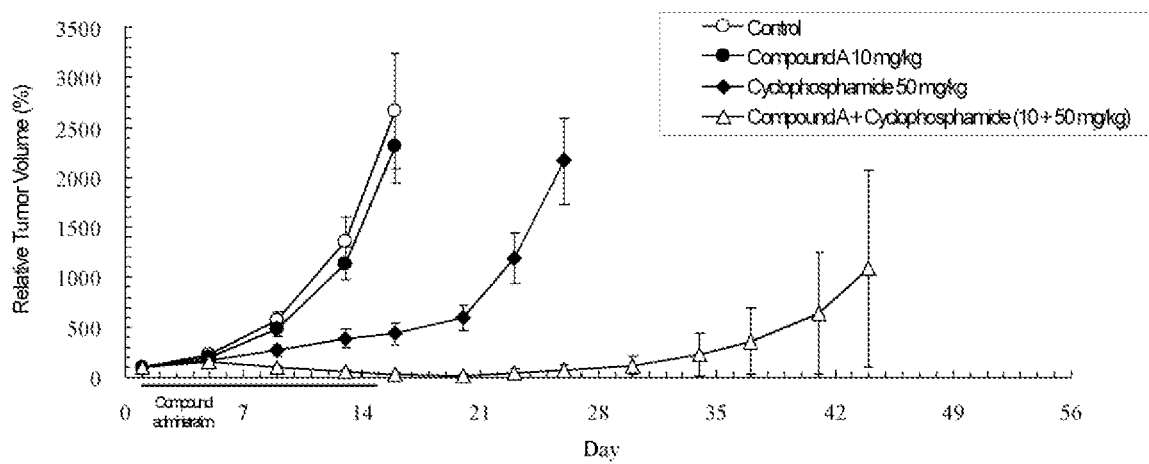

[Fig. 37]
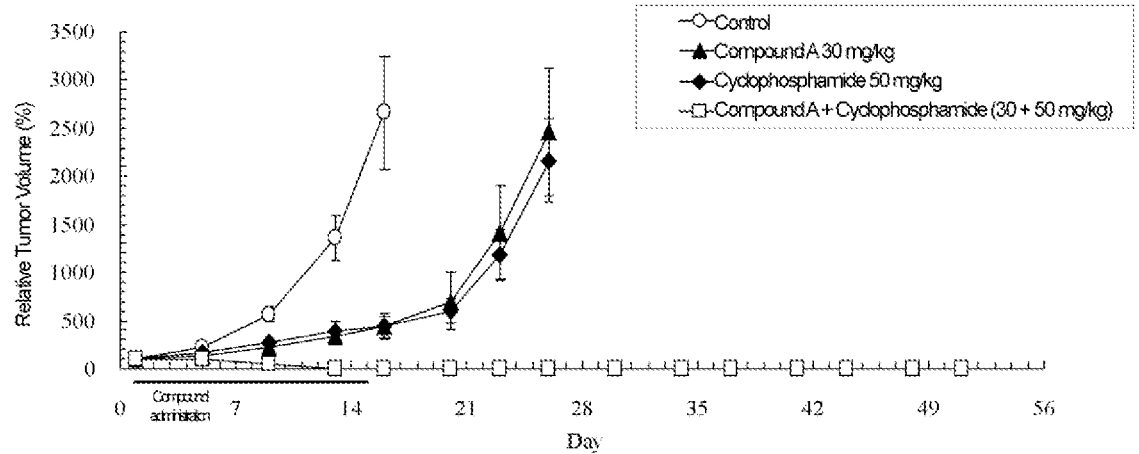
[Fig. 38]
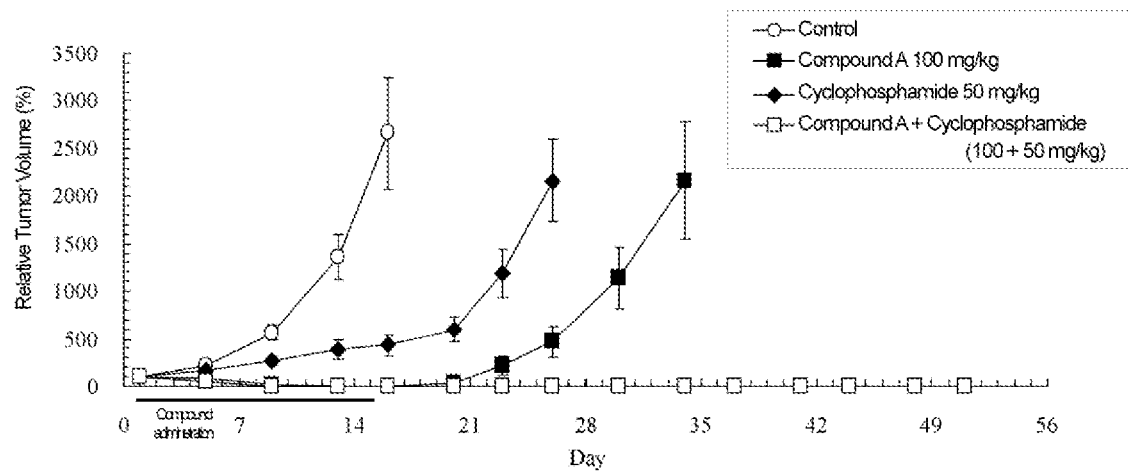

[Fig. 39]
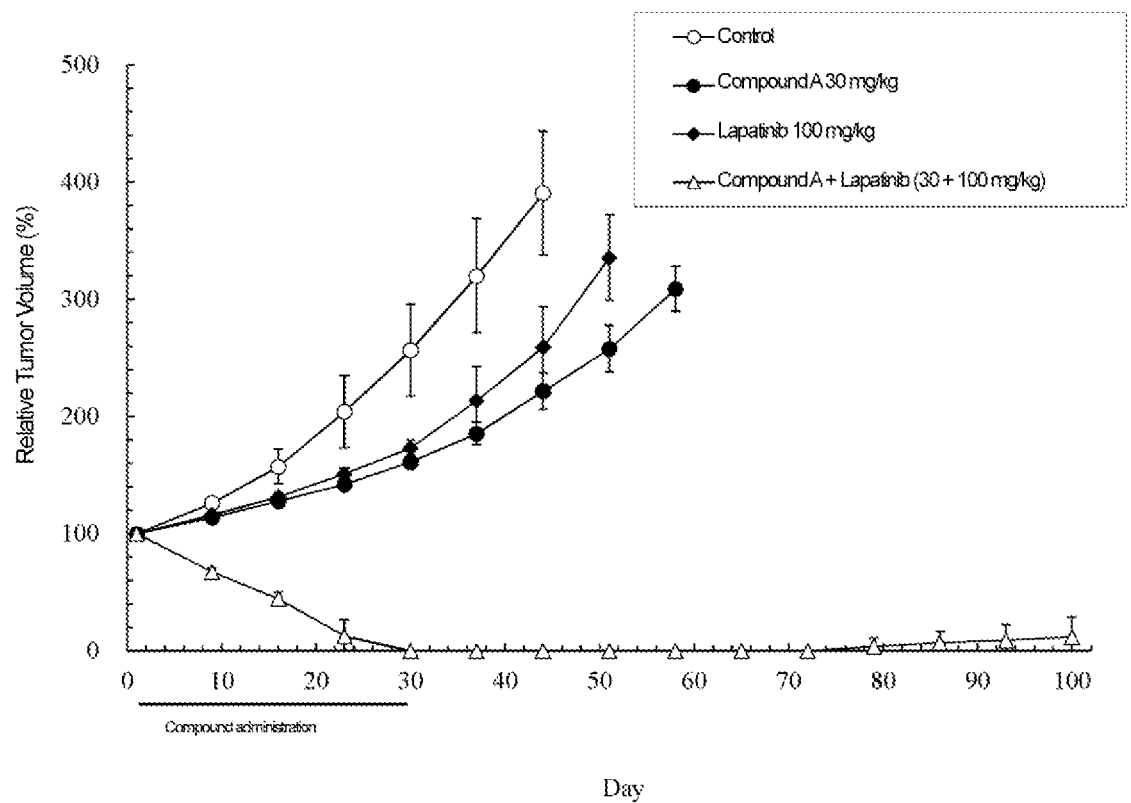

[Fig. 40]
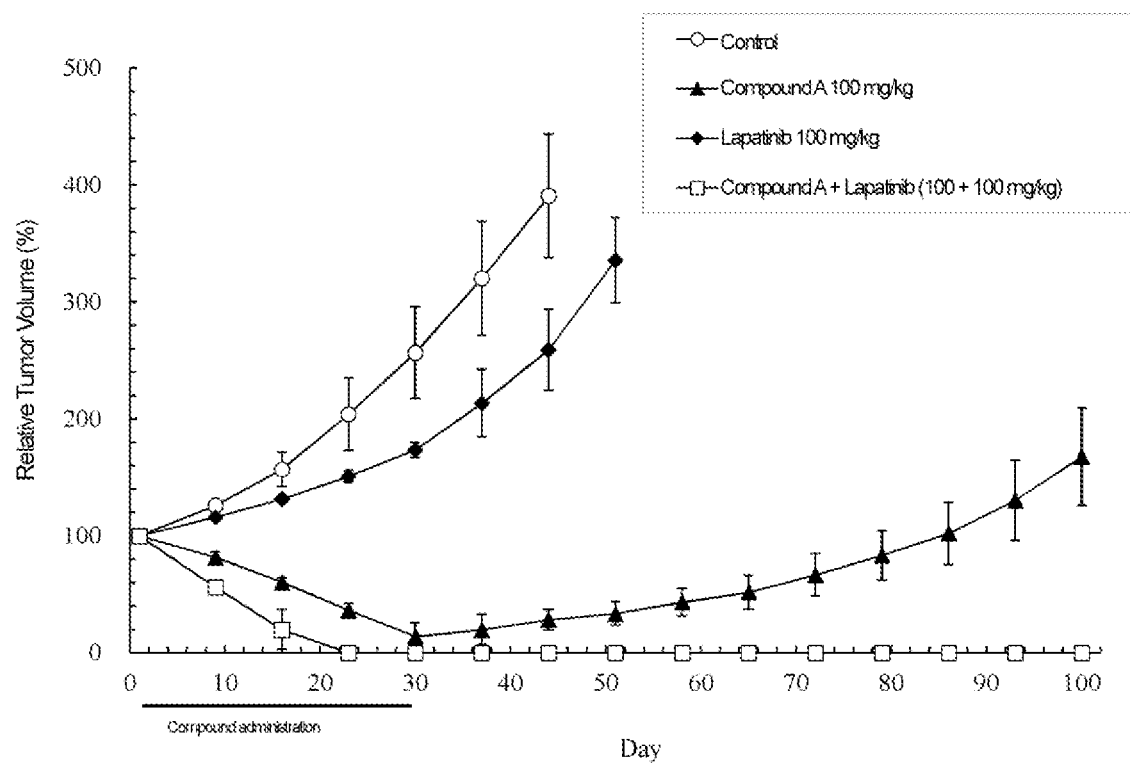

[Fig. 41]
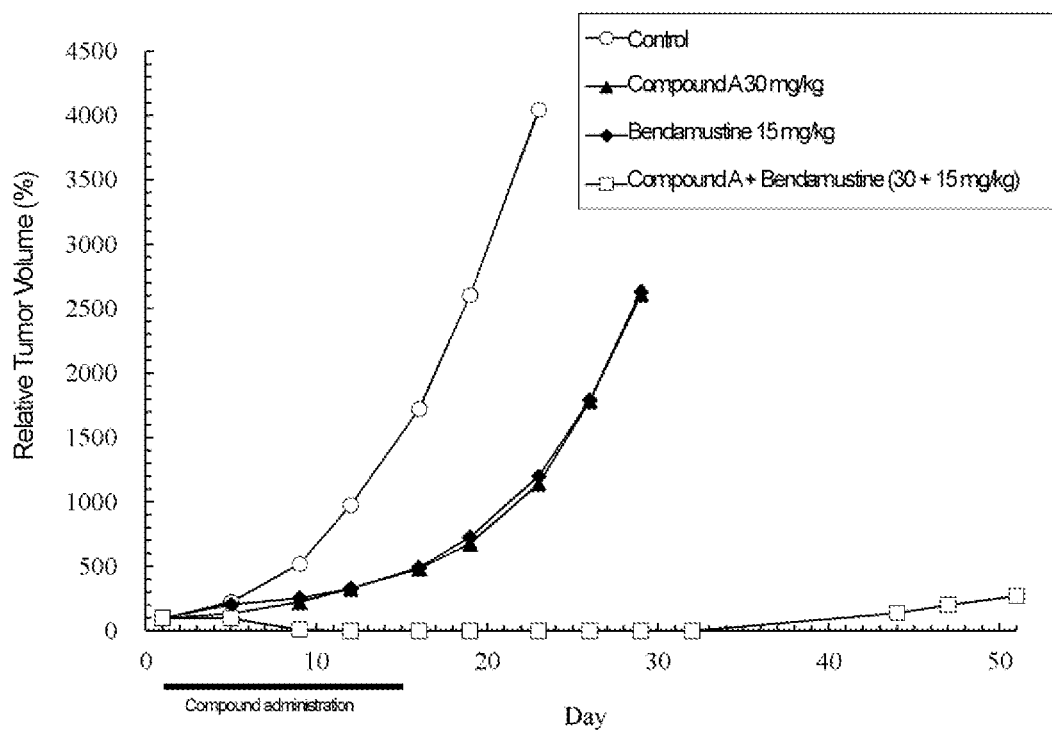
[Fig. 42]
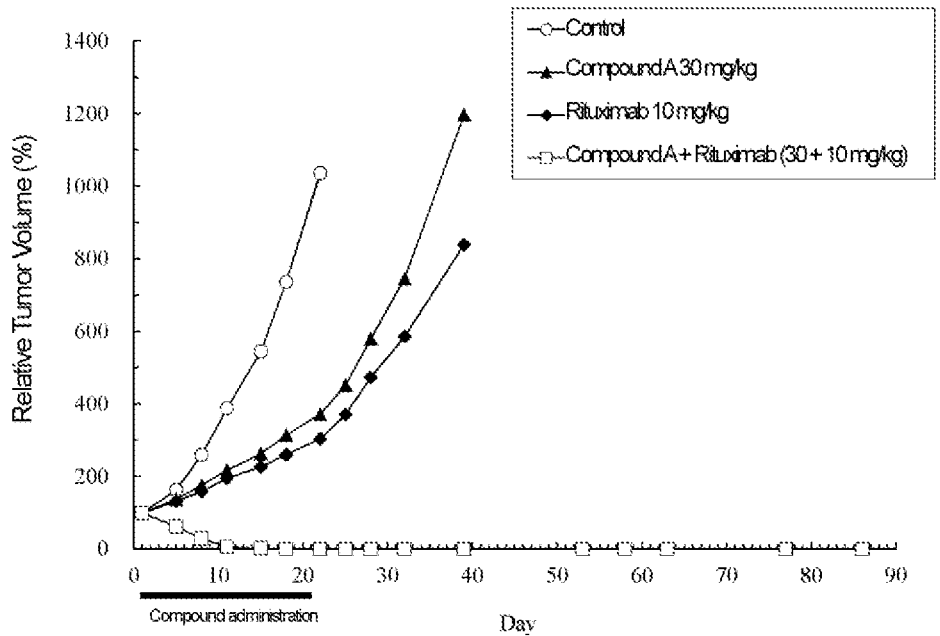

[Fig. 43]
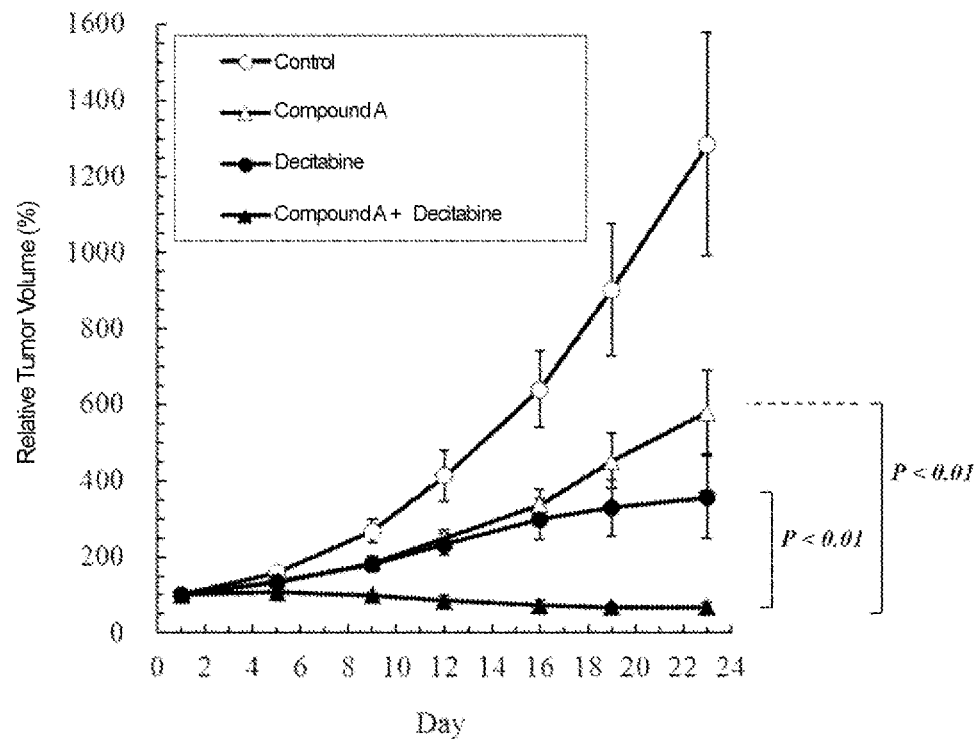
[Fig. 44]
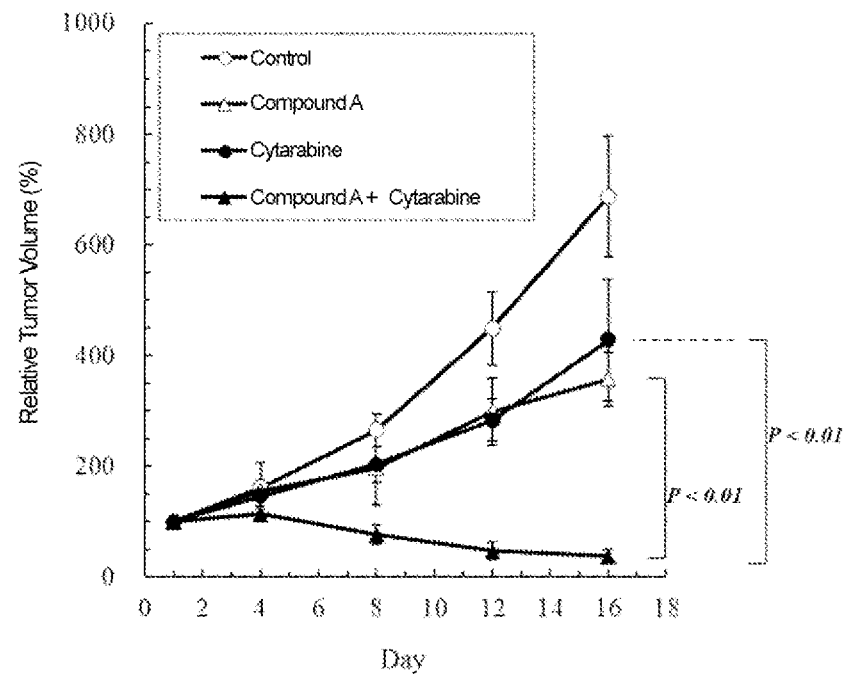

[Fig. 45]
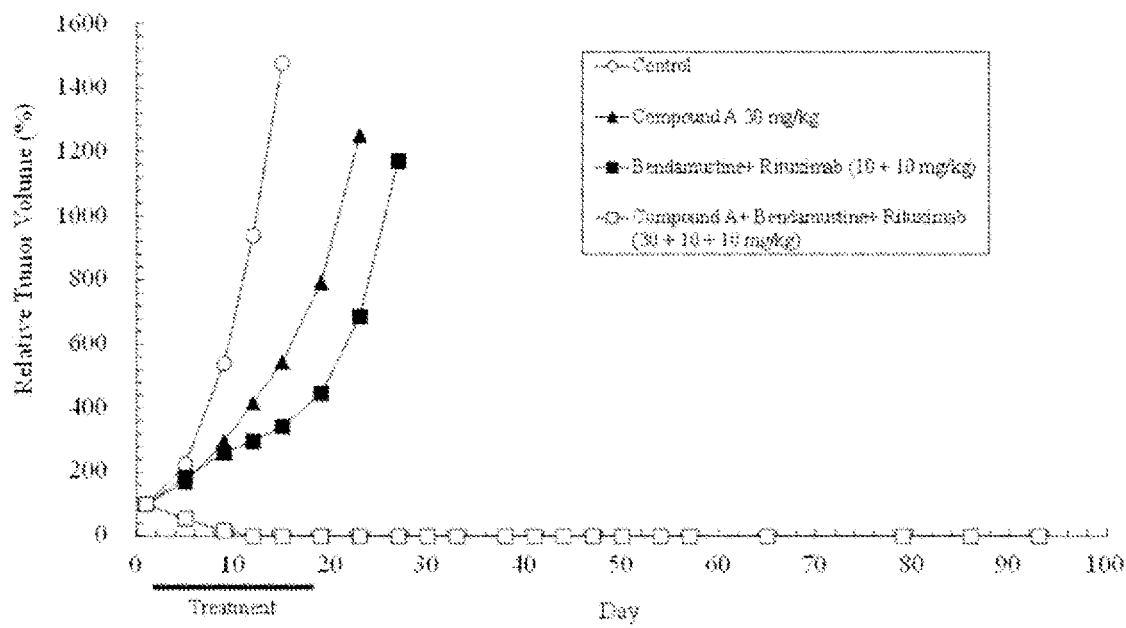
[Fig. 46]
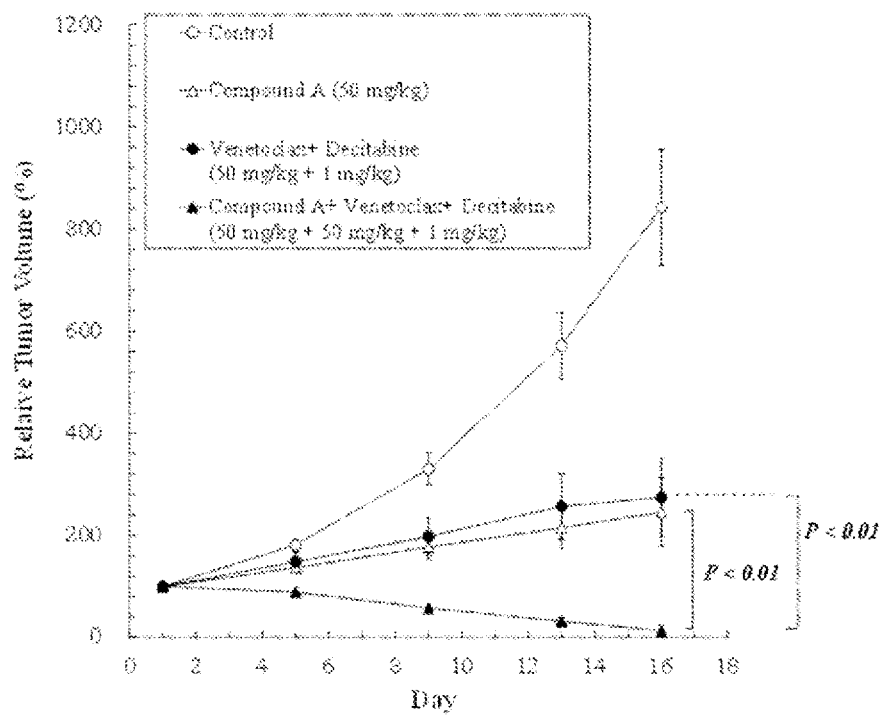

ANTITUMOR COMPOSITION

CROSS REFERENCE TO RELATED APPLICATIONS

This application is a National Stage of International Application No. PCT/JP2020/013454 filed Mar. 25, 2020, claiming priority based on Japanese Patent Application No. 2019-057029 filed Mar. 25, 2019.

TECHNICAL FIELD

The present disclosure relates to an antitumor composition, a method for preventing or treating a tumor, and the like. The entire contents of all of the documents cited in the present specification, including the following prior art documents (Patent Literature and Non-Patent Literature), are incorporated herein by reference.

BACKGROUND ART

The number of people who die from malignant tumors (cancer) is on the rise. Therefore, excellent methods for treating malignant tumors are always desired, and such methods are being developed every day.

CITATION LIST

Patent Literature

[PTL 1]
WO2012/046825

SUMMARY OF INVENTION

Technical Problem

In general, when an antitumor agent is administered alone in the chemotherapy of tumors, particularly malignant tumors, there are limitations in terms of side effects etc. on the exhibition of sufficient antitumor effects. Therefore, multi-drug combination therapy combining two or three or more drugs is performed in a clinical setting. This combination therapy aims to reduce side effects or enhance antitumor action by combining different antitumor agents, for example, 1) to reduce insensitive cell populations, 2) to prevent or delay the emergence of drug resistance, and 3) to disperse toxicity by combining drugs with different toxicity profiles.

However, even if combination therapy is performed by randomly combining different antitumor agents, the effect of enhancing the antitumor action cannot always be obtained. In addition, when a plurality of antitumor agents are used in combination, side effects often increase together with the antitumor action. For this reason, there has been a demand for a novel combination of antitumor agents that can significantly shrink tumors by synergistic antitumor action, without increasing side effects as much as possible.

Solution to Problem

The present inventors found that the combined use of a specific antitumor agent and a specific compound makes it possible to obtain an antitumor effect much higher than antitumor effects obtained by using them alone, and made further improvements.

The present disclosure encompasses, for example, the subject matter described in the following items.

Item 1. An antitumor composition comprising the following compound (B) or a salt thereof for use in combination with the following antitumor agent (A):

(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors;

(B) a compound or a salt thereof represented by the following formula (1):

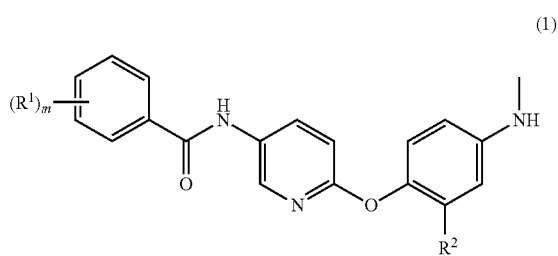

(1)

wherein
$R^1$ represents a halogen atom, an aryl group, an aryloxy group, or a lower alkyl group optionally substituted with one or more halogen atoms;
$R^2$ represents a hydrogen atom, a halogen atom, a lower alkyl group, or a lower alkoxy group; and
m represents an integer of 1 to 3, provided that when m represents 2 or 3, $R^1$ is the same or different.

Item 2. An antitumor composition comprising the following compound (B) or a salt thereof for use in administration to a person who will receive or has received the following antitumor agent (A):

(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors;

(B) a compound or a salt thereof represented by the following formula (1):

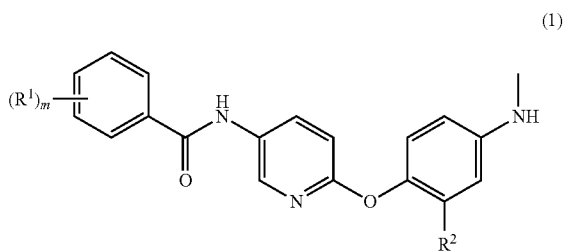

(1)

wherein
$R^1$ represents a halogen atom, an aryl group, an aryloxy group, or a lower alkyl group optionally substituted with one or more halogen atoms;
$R^2$ represents a hydrogen atom, a halogen atom, a lower alkyl group, or a lower alkoxy group; and
m represents an integer of 1 to 3, provided that when m represents 2 or 3, $R^1$ is the same or different.

Item 3. An antitumor composition comprising:
the following antitumor agent (A), and
the following compound (B) or a salt thereof:
(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors;
(B) a compound or a salt thereof represented by the following formula (1):

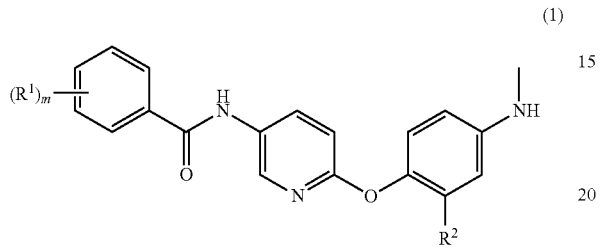

wherein
R¹ represents a halogen atom, an aryl group, an aryloxy group, or a lower alkyl group optionally substituted with one or more halogen atoms;
R² represents a hydrogen atom, a halogen atom, a lower alkyl group, or a lower alkoxy group; and
m represents an integer of 1 to 3, provided that when m represents 2 or 3, R¹ is the same or different.

Item 4. The composition according to any one of Items 1 to 3, wherein compound (B) or a salt thereof is at least one compound or a salt thereof selected from the group consisting of:
N-{6-[2-fluoro-4-(methylamino)phenoxy]pyridin-3-yl}-4-phenoxybenzamide,
N-{6-[2-fluoro-4-(methylamino)phenoxy]pyridin-3-yl}biphenyl-4-carboxamide,
N-{6-[2-fluoro-4-(methylamino)phenoxy]pyridin-3-yl}-4-(trifluoromethyl)benzamide,
2-fluoro-N-{6-[2-fluoro-4-(methylamino)phenoxy]pyridin-3-yl}-4-(trifluoromethyl)benzamide,
2,3,4-trifluoro-N-{6-[2-fluoro-4-(methylamino)phenoxy]pyridin-3-yl}benzamide,
N-{6-[2-methyl-4-(methylamino)phenoxy]pyridin-3-yl}-4-phenoxybenzamide,
N-{6-[2-methyl-4-(methylamino)phenoxy]pyridin-3-yl}biphenyl-4-carboxamide,
N-{6-[2-methyl-4-(methylamino)phenoxy]pyridin-3-yl}-4-(trifluoromethyl)benzamide,
2-fluoro-N-{6-[2-methyl-4-(methylamino)phenoxy]pyridin-3-yl}-4-(trifluoromethyl)benzamide,
N-{6-[4-(methylamino)phenoxy]pyridin-3-yl}-4-phenoxybenzamide,
N-{6-[4-(methylamino)phenoxy]pyridin-3-yl}biphenyl-4-carboxamide,
N-{6-[2-methoxy-4-(methylamino)phenoxy]pyridin-3-yl}-4-(trifluoromethyl)benzamide,
N-{6-[2-methoxy-4-(methylamino)phenoxy]pyridin-3-yl}-4-phenoxybenzamide,
N-{6-[2-methoxy-4-(methylamino)phenoxy]pyridin-3-yl}biphenyl-4-carboxamide,
2-fluoro-N-{6-[2-methoxy-4-(methylamino)phenoxy]pyridin-3-yl}-4-(trifluoromethyl)benzamide,
2,3,4-trifluoro-N-{6-[2-methoxy-4-(methylamino)phenoxy]pyridin-3-yl}benzamide,
2,3,4-trifluoro-N-{6-[2-methyl-4-(methylamino)phenoxy]pyridin-3-yl}benzamide,
N-{6-[4-(methylamino)phenoxy]pyridin-3-yl}-4-(trifluoromethyl)benzamide,
2-fluoro-N-{6-[4-(methylamino)phenoxy]pyridin-3-yl}-4-(trifluoromethyl)benzamide, and
2,3,4-trifluoro-N-{6-[4-(methylamino)phenoxy]pyridin-3-yl}benzamide.

Item 5. A kit comprising:
the following antitumor agent (A), and
an antitumor composition comprising the following compound (B) or a salt thereof:
(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors;
(B) a compound or a salt thereof represented by the following formula (1):

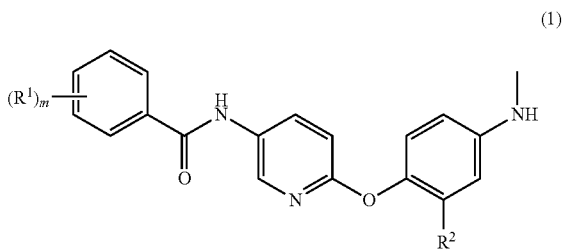

wherein
R¹ represents a halogen atom, an aryl group, an aryloxy group, or a lower alkyl group optionally substituted with one or more halogen atoms;
R² represents a hydrogen atom, a halogen atom, a lower alkyl group, or a lower alkoxy group; and
m represents an integer of 1 to 3, provided that when m represents 2 or 3, R¹ is the same or different.

Item 6. A method for preventing or treating a tumor, the method comprising administering the following antitumor agent (A) and the following compound (B) or a salt thereof to a subject:
(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors;
(B) a compound or a salt thereof represented by the following formula (1):

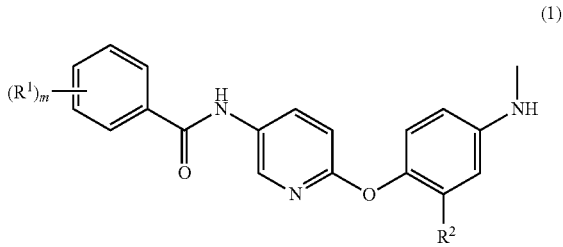

wherein
R¹ represents a halogen atom, an aryl group, an aryloxy group, or a lower alkyl group optionally substituted with one or more halogen atoms;

R² represents a hydrogen atom, a halogen atom, a lower alkyl group, or a lower alkoxy group; and m represents an integer of 1 to 3, provided that when m represents 2 or 3, R¹ is the same or different.

Item 7. The following compound (B) or a salt thereof for use in combination with the following antitumor agent (A) in the prevention or treatment of a tumor:

(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors;

(B) a compound or a salt thereof represented by the following formula (1):

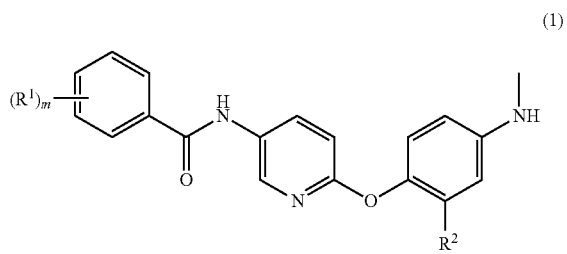

(1)

wherein

R¹ represents a halogen atom, an aryl group, an aryloxy group, or a lower alkyl group optionally substituted with one or more halogen atoms;

R² represents a hydrogen atom, a halogen atom, a lower alkyl group, or a lower alkoxy group; and m represents an integer of 1 to 3, provided that when m represents 2 or 3, R¹ is the same or different.

Item 8. The composition according to any one of Items 1 to 4, the kit according to Item 5, the prevention or treatment method according to Item 6, or the compound or a salt thereof according to Item 7, wherein antitumor agent (A) is at least one member selected from the group consisting of:

compounds having 2 or 3 or more alkyl group moieties capable of covalently binding to DNA bases, anti-CD20 antibodies or fragments thereof that recognize CD20 antigen, aptamers that recognize CD20 antigen, or complex molecules comprising them (preferably antibody-drug conjugates (ADCs)), DNA methyltransferase inhibitors, pyrimidine antimetabolites, purine antimetabolites, antifolates, Bcl-2 inhibitors, and tyrosine kinase inhibitors.

Item 9. The composition according to any one of Items 1 to 4, the kit according to Item 5, the prevention or treatment method according to Item 6, or the compound or a salt thereof according to Item 7, wherein antitumor agent (A) is at least one member selected from the group consisting of:

nitrogen mustards (e.g., mechlorethamine hydrochloride, cyclophosphamide, ifosfamide, melphalan, chlorambucil, and bendamustine), aziridines and epoxides (e.g., thiotepa, mitomycin C, and dianhydrogalactitol), alkyl sulfonates (e.g., busulfan), nitrosoureas (e.g., carmustine, lomustine, and ranimustine), hydrazine and triazene derivatives (e.g., procarbazine, dacarbazine, and temozolomide), rituximab, ibritumomab, antibodies that have been confirmed to be comparable with rituximab or ibritumomab (biosimilars of rituximab or ibritumomab), ibritumomab tiuxetan, decitabine, azacitidine, and zebularine, cytarabine, 5-FU (5-fluorouracil), azathioprine, mercaptopurine, and methotrexate, venetoclax, and lapatinib, gefitinib, imatinib, ponatinib, erlotinib, ibrutinib, axitinib, lenvatinib, afatinib, and gilteritinib.

Advantageous Effects of Invention

The combined use of a specific antitumor agent and a specific compound makes it possible to obtain an antitumor effect much higher than antitumor effects obtained by using them alone.

BRIEF DESCRIPTION OF DRAWINGS

FIG. 1 shows isobologram analysis results showing the combination effect of N-{6-[2-methyl-4-(methylamino)phenoxy]pyridin-3-yl}-4-(trifluoromethyl)benzamide hydrochloride (hereinafter also referred to as "compound A" in the Brief Description of Drawings) and bendamustine on human follicular lymphoma cell line DOHH-2.

FIG. 2 shows isobologram analysis results showing the combination effect of compound A and bendamustine on human breast cancer cell line MDA-MB-231.

FIG. 3 shows isobologram analysis results showing the combination effect of compound A and decitabine on human acute myelogenous leukemia (AML) cell line CMK-86.

FIG. 4 shows isobologram analysis results showing the combination effect of compound A and busulfan on human acute myelogenous leukemia (AML) cell line MV-4-11.

FIG. 5 shows isobologram analysis results showing the combination effect of compound A and lomustine on human chronic myelogenous leukemia (CML) cell line K562.

FIG. 6 shows isobologram analysis results showing the combination effect of compound A and thiotepa on human lung cancer cell line A549.

FIG. 7 shows isobologram analysis results showing the combination effect of compound A and lomustine on human pancreatic cancer cell line BxPC-3.

FIG. 8 shows isobologram analysis results showing the combination effect of compound A and melphalan on human acute myelogenous leukemia (AML) cell line KG-1.

FIG. 9 shows isobologram analysis results showing the combination effect of compound A and lomustine on human diffuse large B-cell lymphoma (DLBCL) cell line U2932.

FIG. 10 shows isobologram analysis results showing the combination effect of compound A and melphalan on human diffuse large B-cell lymphoma (DLBCL) cell line U2932.

FIG. 11 shows isobologram analysis results showing the combination effect of compound A and melphalan on human acute myelogenous leukemia (AML) cell line MV-4-11.

FIG. 12 shows isobologram analysis results showing the combination effect of compound A and lomustine on human gastric cancer cell line MKN45.

FIG. 13 shows isobologram analysis results showing the combination effect of compound A and decitabine on human acute myelogenous leukemia (AML) cell line MV-4-11.

FIG. 14 shows isobologram analysis results showing the combination effect of compound A and decitabine on human acute myelogenous leukemia (AML) cell line OCI-AML2.

FIG. 15 shows isobologram analysis results showing the combination effect of compound A and cytarabine on human acute myelogenous leukemia (AML) cell line MV-4-11.

FIG. 16 shows isobologram analysis results showing the combination effect of compound A and bendamustine on human breast cancer cell line BT-474.

FIG. 17 shows isobologram analysis results showing the combination effect of compound A and melphalan on human multiple myeloma cell line RPMI 8226.

FIG. 18 shows isobologram analysis results showing the combination effect of compound A and venetoclax on human acute myelogenous leukemia (AML) cell line KG-1.

FIG. 19 shows isobologram analysis results showing the combination effect of compound A and ranimustine on human chronic myelogenous leukemia (CML) cell line K562.

FIG. 20 shows isobologram analysis results showing the combination effect of compound A and thiotepa on human ovarian cancer cell line SK-OV-3.

FIG. 21 shows isobologram analysis results showing the combination effect of compound A and ibrutinib on human acute myelogenous leukemia (AML) cell line MV-4-11.

FIG. 22 shows isobologram analysis results showing the combination effect of compound A and decitabine on human myelodysplastic syndrome cell line SKM-1.

FIG. 23 shows isobologram analysis results showing the combination effect of compound A and erlotinib on human lung cancer cell line A549.

FIG. 24 shows isobologram analysis results showing the combination effect of compound A and gefitinib on human lung cancer cell line A549.

FIG. 25 shows isobologram analysis results showing the combination effect of compound A and gefitinib on human lung cancer cell line HCC 827.

FIG. 26 shows isobologram analysis results showing the combination effect of compound A and imatinib on human chronic myelogenous leukemia (CML) cell line K562.

FIG. 27 shows isobologram analysis results showing the combination effect of compound A and axitinib on human renal cancer cell line ACHN.

FIG. 28 shows isobologram analysis results showing the combination effect of compound A and lapatinib on human breast cancer cell line MDA-MB-453.

FIG. 29 shows isobologram analysis results showing the combination effect of compound A and lenvatinib on human hepatoma cell line Hep G2.

FIG. 30 shows isobologram analysis results showing the combination effect of compound A and lapatinib on human breast cancer cell line SK-BR-3.

FIG. 31 shows isobologram analysis results showing the combination effect of compound A and afatinib on human lung cancer cell line A549.

FIG. 32 shows isobologram analysis results showing the combination effect of compound A and gilteritinib on human acute myelogenous leukemia (AML) cell line MV-4-11.

FIG. 33 shows isobologram analysis results showing the combination effect of compound A and 5-FU on human head and neck (pharyngeal) cancer cell line FaDu.

FIG. 34 shows isobologram analysis results showing the combination effect of compound A and vincristine on human diffuse large B-cell lymphoma cell line OCI-Ly18.

FIG. 35 shows isobologram analysis results showing the combination effect of compound A and docetaxel on human breast cancer cell line BT-474.

FIG. 36 shows the results of the combination effect of compound A and cyclophosphamide on human diffuse large B-cell lymphoma cell line OCI-Ly7.

FIG. 37 shows the results of the combination effect of compound A and cyclophosphamide on human diffuse large B-cell lymphoma cell line OCI-Ly7.

FIG. 38 shows the results of the combination effect of compound A and cyclophosphamide on human diffuse large B-cell lymphoma cell line OCI-Ly7.

FIG. 39 shows the results of the combination effect of compound A and lapatinib on human breast cancer cell line MDA-MB-453.

FIG. 40 shows the results of the combination effect of compound A and lapatinib on human breast cancer cell line MDA-MB-453.

FIG. 41 shows the results of the combination effect of compound A and bendamustine on human diffuse large B-cell lymphoma cell line OCI-Ly7.

FIG. 42 shows the results of the combination effect of compound A and rituximab on human diffuse large B-cell lymphoma cell line OCI-Ly7.

FIG. 43 shows the results of the combination effect of compound A and decitabine on human acute myelogenous leukemia (AML) cell line KG-1.

FIG. 44 shows the results of the combination effect of compound A and cytarabine on human acute myelogenous leukemia (AML) cell line KG-1.

FIG. 45 shows the results of the three-drug combination effect of compound A, bendamustine, and rituximab on human diffuse large B-cell lymphoma cell line OCI-Ly7.

FIG. 46 shows the results of the three-drug combination effect of compound A, decitabine, and venetoclax on human acute myelogenous leukemia (AML) cell line KG-1.

DESCRIPTION OF EMBODIMENTS

Each of the embodiments included in the present disclosure are described in more detail below. The present disclosure preferably includes an antitumor composition, a method for preventing or treating a tumor, an antitumor kit, etc.; however, the present disclosure is not limited thereto. The present disclosure includes all of the embodiments disclosed herein and recognized by those skilled in the art.

The antitumor composition included in the present disclosure comprises the following compound (B) or a salt thereof. Hereinafter, the antitumor composition comprising compound (B) or a salt thereof is also referred to as "the antitumor composition of the present disclosure."

(B) A compound or a salt thereof represented by the following formula (1):

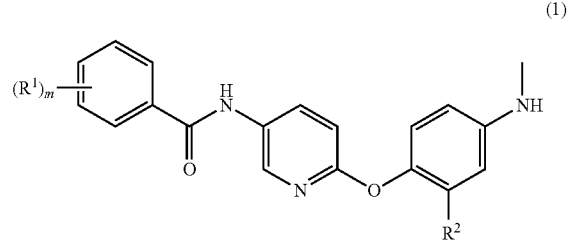

wherein
$R^1$ represents a halogen atom, an aryl group, an aryloxy group, or a lower alkyl group optionally substituted with one or more halogen atoms;
$R^2$ represents a hydrogen atom, a halogen atom, a lower alkyl group, or a lower alkoxy group; and
m represents an integer of 1 to 3, provided that when m represents 2 or 3, $R^1$ is the same or different.

Specific examples of the individual groups shown in formula (1) are as follows.

Examples of lower alkoxy groups include linear or branched alkoxy groups having 1 to 6 carbon atoms, such as methoxy, ethoxy, propoxy, isopropoxy, butoxy, tert-butoxy, pentyloxy, and hexyloxy groups.

Examples of lower alkyl groups include linear or branched alkyl groups having 1 to 6 carbon atoms, such as methyl, ethyl, propyl, isopropyl, 2,2-dimethylpropyl, 1-ethylpropyl, butyl, isobutyl, tert-butyl, isopentyl, pentyl, and hexyl groups.

Examples of lower alkyl groups optionally substituted with one or more halogen atoms include, in addition to the lower alkyl groups mentioned above, linear or branched alkyl groups having 1 to 6 carbon atoms that may be substituted with 1 to 3 halogen atoms, such as trifluoromethyl, trichloromethyl, chloromethyl, bromomethyl, fluoromethyl, iodomethyl, difluoromethyl, dibromomethyl, dichloromethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of halogen atoms include fluorine, chlorine, bromine, and iodine atoms.

Examples of aryl groups include $C_6$-$C_{10}$ aromatic groups, such as phenyl, 1-naphthyl, 2-naphthyl, o-tolyl, m-tolyl, and p-tolyl groups.

Examples of aryloxy groups include $C_6$-$C_{10}$ aryloxy groups, such as phenoxy, 1-naphthyloxy, and 2-naphthyloxy groups.

A preferred example is a compound or a salt thereof represented by formula (1), wherein:
$R^1$ represents an aryl group, an aryloxy group, or a lower alkyl group optionally substituted with one or more halogen atoms;
$R^2$ represents a hydrogen atom, a halogen atom, a lower alkyl group, or a lower alkoxy group; and
m represents an integer of 1.

Another preferred example is a compound or a salt thereof represented by formula (1), wherein:
$R^1$ represents a halogen atom;
$R^2$ represents a hydrogen atom, a halogen atom, a lower alkyl group, or a lower alkoxy group; and
m represents an integer of 1 to 3;
provided that when m represents 2 or 3, $R^1$ is the same or different.

Further another preferred example is a compound or a salt thereof represented by formula (1), wherein:
$R^1$ represents halogen or a lower alkyl group optionally substituted with one or more halogen atoms;
$R^2$ represents a hydrogen atom, a halogen atom, a lower alkyl group, or a lower alkoxy group; and
m represents an integer of 2;
provided that $R^1$ is the same or different.

More specific preferred examples of the compound represented by formula (1) include:
N-(6-[2-fluoro-4-(methylamino)phenoxy]pyridin-3-yl)-4-phenoxybenzamide,
N-(6-[2-fluoro-4-(methylamino)phenoxy]pyridin-3-yl)biphenyl-4-carboxamide,
N-{6-[2-fluoro-4-(methylamino)phenoxy]pyridin-3-yl}-4-(trifluoromethyl)benzamide,
2-fluoro-N-{6-[2-fluoro-4-(methylamino)phenoxy]pyridin-3-yl}-4-(trifluoromethyl)benzamide,
2,3,4-trifluoro-N-{6-[2-fluoro-4-(methylamino)phenoxy]pyridin-3-yl}benzamide,
N-{6-[2-methyl-4-(methylamino)phenoxy]pyridin-3-yl}-4-phenoxybenzamide,
N-(6-[2-methyl-4-(methylamino)phenoxy]pyridin-3-yl)biphenyl-4-carboxamide,
N-{6-[2-methyl-4-(methylamino)phenoxy]pyridin-3-yl}-4-(trifluoromethyl)benzamide,
2-fluoro-N-{6-[2-methyl-4-(methylamino)phenoxy]pyridin-3-yl}-4-(trifluoromethyl)benzamide,
N-{6-[4-(methylamino)phenoxy]pyridin-3-yl}-4-phenoxybenzamide,
N-{6-[4-(methylamino)phenoxy]pyridin-3-yl}biphenyl-4-carboxamide,
N-{6-[2-methoxy-4-(methylamino)phenoxy]pyridin-3-yl}-4-(trifluoromethyl)benzamide,
N-{6-[2-methoxy-4-(methylamino)phenoxy]pyridin-3-yl}-4-phenoxybenzamide,
N-{6-[2-methoxy-4-(methylamino)phenoxy]pyridin-3-yl}biphenyl-4-carboxamide,
2-fluoro-N-{6-[2-methoxy-4-(methylamino)phenoxy]pyridin-3-yl}-4-(trifluoromethyl)benzamide,
2,3,4-trifluoro-N-{6-[2-methoxy-4-(methylamino)phenoxy]pyridin-3-yl}benzamide,
2,3,4-trifluoro-N-{6-[2-methyl-4-(methylamino)phenoxy]pyridin-3-yl}benzamide,
N-{6-[4-(methylamino)phenoxy]pyridin-3-yl}-4-(trifluoromethyl)benzamide,
2-fluoro-N-{6-[4-(methylamino)phenoxy]pyridin-3-yl}-4-(trifluoromethyl)benzamide, and
2,3,4-trifluoro-N-{6-[4-(methylamino)phenoxy]pyridin-3-yl}benzamide.

Salts of these compounds can also be preferably used.

Examples of the salt of the compound represented by formula (1) include inorganic acid salts, such as sulfate, nitrate, hydrochloride, phosphate, and hydrobromide; and organic acid salts, such as acetate, sulfonate (e.g., p-toluene sulfonate, methane sulfonate, and ethane sulfonate), oxalate, maleate, fumarate, malate, tartrate, citrate, succinate, and benzoate.

The compound or a salt thereof represented by formula (1) can be prepared by a known method or a method easily conceivable from a known method. For example, the method described in PTL 1 (WO2012/046825) can be used for preparation.

The antitumor composition of the present disclosure is used in combination with the following antitumor agent (A):
(A) at least one antitumor agent selected from the group consisting of alkylating agents, CD20 recognition molecules, DNA methylation inhibitors, pyrimidine antimetabolites, purine antimetabolites, antifolates, Bcl-2 inhibitors, and tyrosine kinase inhibitors.

Alkylating agents are a type of cytotoxic anticancer drugs (carcinostatic drugs). They have multiple alkyl group moieties capable of covalently binding to DNA bases, and prevent DNA replication by linking two DNA strands (interstrand cross-linking). DNA bases, particularly guanine, are nucleophilic. In general, a DNA base and an alkyl group are covalently bonded by a nucleophilic substitution reaction. The alkylating agent is preferably one having two or three or more alkyl group moieties. More specific examples include nitrogen mustards (e.g., mechlorethamine hydrochloride, cyclophosphamide, ifosfamide, melphalan, chlorambucil, and bendamustine), aziridines and epoxides (e.g., thiotepa, mitomycin C, and dianhydrogalactitol), alkyl sulfonates (e.g., busulfan), nitrosoureas (e.g., carmustine, lomustine, and ranimustine), hydrazine and triazene derivatives (e.g., procarbazine, dacarbazine, and temozolomide), and the like.

The CD20 recognition molecules mentioned herein are molecules that recognize CD20 antigen (Bp35) and that have an antitumor effect. Examples include anti-CD20 antibodies or fragments thereof that recognize CD20 antigen, aptamers that recognize CD20 antigen, and complex molecules comprising them. The antibodies may be either polyclonal antibodies or monoclonal antibodies; however, monoclonal antibodies are preferable. Further, preferable antibodies are chimeric antibodies (chimeras of a rodent (e.g., a mouse, rat, or Chinese hamster) and a human), humanized antibodies, and fully humanized antibodies. Preferred examples of anti-CD20 antibodies include rituximab, ibritumomab, antibodies that have been confirmed to be comparable with rituximab or ibritumomab (biosimilars of rituximab or ibritumomab), and the like. Further, specific examples of the complex molecules mentioned herein preferably include antibody-drug conjugates (ADCs). The antibody-drug conjugate is preferably a conjugate in which an antibody is linked to an anticancer agent via a linker. Examples of the antibody-drug conjugate (ADC) include ibritumomab tiuxetan, in which an antibody is linked to a compound containing a radioisotope (tiuxetan).

The DNA methylation inhibitor is preferably a DNA methyltransferase inhibitor. More specific examples include decitabine, azacitidine, zebularine, and the like.

The antimetabolite is preferably a pyrimidine antimetabolite, a purine antimetabolite, or an antifolate. More specifically, examples of pyrimidine antimetabolites include cytarabine and 5-FU (5-fluorouracil); examples of purine antimetabolites include azathioprine and mercaptopurine; and examples of antifolates include methotrexate.

Bcl-2 (B-cell lymphoma 2) is known as an oncogene that regulates apoptosis by regulating mitochondrial membrane permeability. Examples of Bcl-2 inhibitors include venetoclax.

Examples of tyrosine kinase inhibitors include lapatinib, gefitinib, imatinib, ponatinib, erlotinib, ibrutinib, axitinib, lenvatinib, afatinib, gilteritinib, and the like.

The antitumor composition of the present disclosure can be prepared by combining compound (B) or a salt thereof with, for example, a pharmaceutically acceptable carrier. The preparation can be performed by a known method or a method easily conceivable from a known method.

The antitumor composition of the present disclosure is preferably used in the form of a general pharmaceutical preparation. Such pharmaceutical preparations are obtained by formulation using commonly used excipients or additives, such as fillers, extenders, binders, wetting agents, disintegrants, surfactants, and lubricants.

The form of the pharmaceutical preparation can be selected from various forms depending on the treatment purpose. Typical examples include tablets, pills, powders, solutions, suspensions, emulsions, granules, capsules, suppositories, injections (e.g., solutions and suspensions), and the like.

To form tablets, various known carriers can be used. Examples of the carriers include lactose, sucrose, sodium chloride, glucose, urea, starch, calcium carbonate, kaolin, crystalline cellulose, and other additives; water, ethanol, propanol, simple syrup, glucose solutions, starch solutions, gelatin solutions, carboxymethyl cellulose, shellac, methyl cellulose, potassium phosphate, polyvinylpyrrolidone, and other binders; dry starch, sodium alginate, agar powder, laminaran powder, sodium hydrogen carbonate, calcium carbonate, fatty acid esters of polyoxyethylene sorbitan, sodium lauryl sulfate, stearic acid monoglyceride, starch, lactose, and other disintegrants; sucrose, stearin, cocoa butter, hardened oil, and other disintegration inhibitors; quaternary ammonium bases, sodium lauryl sulfate, and other absorption enhancers; glycerin, starch, and other wetting agents; starch, lactose, kaolin, bentonite, colloidal silicic acid, and other adsorbents; purified talc, stearate, boric acid powder, polyethylene glycol, and other lubricants.

Such tablets may be coated with known coating materials, if necessary, in the case of, for example, preparing sugar-coated tablets, gelatin-coated tablets, enteric-coated tablets, film-coated tablets, bilayer or multilayer tablets, and the like.

To form pills, various known carriers can be used. Examples of the carriers include glucose, lactose, starch, cocoa butter, hydrogenated vegetable oil, kaolin, talc, and other additives; gum arabic powder, tragacanth powder, gelatin, ethanol, and other binders; laminaran, agar, and other disintegrants.

To form suppositories, various known carriers can be used. Examples of the carriers include polyethylene glycol, cocoa butter, higher alcohols, higher alcohol esters, gelatin, semi-synthetic glyceride, and the like.

To form injections, solutions, emulsions, or suspensions are sterilized and preferably made isotonic with blood. Various known and widely used excipients can be used to prepare solutions, emulsions, or suspensions. Examples of such excipients include water, ethanol, propylene glycol, ethoxylated isostearyl alcohol, polyoxylated isostearyl alcohol, fatty acid esters of polyoxyethylene sorbitan, and the like. In this case, the pharmaceutical preparation may contain sodium chloride, glucose, or glycerin in an amount sufficient to prepare an isotonic solution, and may contain common solubilizing agents, buffers, soothing agents, and the like. Further, the pharmaceutical preparation may contain, if necessary, coloring agents, preservatives, flavoring agents, sweetening agents, and/or other medicines.

The amount of compound (B) or a salt thereof contained in the antitumor composition of the present disclosure is not particularly limited, and is suitably selected from a wide range. For example, the amount of compound (B) or a salt thereof in the composition is about 0.1 to 70 wt %, and preferably about 0.1 to 30 wt %.

The route of administration of the antitumor composition of the present disclosure is not limited. For example, the antitumor composition can be administered by a route suitable for the form of the preparation, the age and sex of the patient, the condition of the disease, and other conditions. For example, tablets, pills, solutions, suspensions, emulsions, granules, and capsules are administered orally. Injections are administered intravenously alone or in admixture with common injection infusions, such as glucose solutions and amino acid solutions; or administered alone intramuscularly, intradermally, subcutaneously, or intraperitoneally, as needed. Suppositories are administered rectally.

The dose of the antitumor composition of the present disclosure can be suitably set according to the method of use, the age and sex of the patient, the severity of the disease, the dose and administration time of antitumor agent (A), and other conditions. Although it is not particularly limited, the dose of the antitumor composition is, for example, 0.001 mg/kg body weight/day to 100 mg/kg body weight/day, and preferably 0.001 mg/kg body weight/day to 50 mg/kg body weight/day, as a single dose or divided doses.

The mode of combination of the antitumor composition of the present disclosure and antitumor agent (A) is not particularly limited. More specifically, for example, the antitumor composition of the present disclosure may be, for example, (i) an antitumor composition for use in combination with antitumor agent (A), (ii) an antitumor composition used for administration to a person who will receive or has received antitumor agent (A), or (iii) an antitumor composition further comprising antitumor agent (A).

Antitumor composition (i) includes all of the embodiments in which it is used in combination with antitumor agent (A). For example, an embodiment in which antitumor composition (i) is used for administration to a person who will receive or has received antitumor agent (A) is included. In other words, antitumor composition (i) includes antitumor composition (ii). In addition, for example, antitumor composition (i) also includes an embodiment in which it is mixed with antitumor agent (A) to prepare an antitumor composition comprising not only compound (B) or a salt thereof, but also antitumor agent (A). In other words, antitumor composition (i) includes a composition for preparing antitumor composition (iii). In addition, for example, antitumor composition (i) also includes an embodiment in which it is used as a collective kit together with antitumor agent (A). In other words, antitumor composition (i) includes an embodiment in which it is used, together with antitumor agent (A), to construct a kit (in particular, an antitumor kit).

Antitumor composition (ii) is used for administration to a person who will receive or has received antitumor agent (A). The person who will receive antitumor agent (A) in this case is a person who receives antitumor agent (A) after or simultaneously with the administration of the antitumor composition of the present disclosure. Further, the person who has received antitumor agent (A) in this case is a person who receives antitumor agent (A) before the administration of the antitumor composition of the present disclosure. In any of these cases, the time interval between the administration of the antitumor composition of the present disclosure and the administration of antitumor agent (A) is not particularly limited, as long as antitumor agent (A) and the antitumor composition of the present disclosure are administered in combination to produce a synergistic effect for tumor treatment. For example, no time interval may be provided (i.e., simultaneous administration), one administration may be started during the other administration, one administration may be started immediately after the completion of the other administration, one administration may be started several minutes to several tens of minutes after the completion of the other administration, or one administration may be started, for example, about 1 to 12 (1, 2, 3, 4, 5, 6, 7, 8, 9, 10, 11, or 12) hours after the completion of the other administration.

Antitumor composition (iii) is an antitumor composition comprising not only compound (B) or a salt thereof, but also antitumor agent (A). The dosage form of the antitumor composition can be suitably set in consideration of the dosage form of antitumor agent (A) and the like. For example, it can be prepared by mixing compound (B) or a salt thereof with antitumor agent (A) or during the preparation of antitumor agent (A). Therefore, the dosage form of antitumor composition (iii) is preferably the same as the dosage form of antitumor agent (A) used for the preparation.

The present disclosure also includes a kit comprising antitumor agent (A) and an antitumor composition comprising compound (B) or a salt thereof. The kit is also referred to as "the kit of the present disclosure." The kit of the present disclosure is preferably an antitumor kit (i.e., a kit for preventing or treating a tumor). Further, in addition to antitumor agent (A) and the antitumor composition comprising compound (B) or a salt thereof, the kit may suitably comprise a medicine more preferable for preventing or treating tumors, an administration device (e.g., a syringe), instructions (an attached document), or the like.

The present disclosure also includes a method for preventing or treating a tumor, the method comprising administering antitumor agent (A) and compound (B) or a salt thereof to a subject. The prevention or treatment method is also referred to as "the prevention or treatment method of the present disclosure." The prevention or treatment method of the present disclosure includes a method for preventing or treating a tumor, comprising separately administering antitumor agent (A) and an antitumor composition comprising compound (B) or a salt thereof, and a method for preventing or treating a tumor, comprising administering antitumor composition (iii). In the former method (method for preventing or treating a tumor, comprising separate administration), the administration schedule of antitumor agent (A) and the antitumor composition comprising compound (B) or a salt thereof is not particularly limited, as long as antitumor agent (A) and the antitumor composition of the present disclosure are administered in combination to produce a synergistic effect for tumor treatment. For example, no time interval may be provided (i.e., simultaneous administration), one administration may be started during the other administration, one administration may be started immediately after the completion of the other administration, one administration may be started several minutes to several tens of minutes after the completion of the other administration, or one administration may be started, for example, about 1 to 12 (1, 2, 3, 4, 5, 6, 7, 8, 9, 10, 11, or 12) hours after the completion of the other administration. One administration may be before or after the other administration.

Further, the subject is not particularly limited, as long as tumor treatment is required.

In the present disclosure, the tumor is a disease caused by abnormal cell proliferation, and is preferably a malignant tumor (cancer). More specific examples include breast cancer (e.g., invasive ductal carcinoma, ductal carcinoma in situ, and inflammatory breast cancer), prostate cancer (e.g., hormone-dependent prostate cancer and hormone-independent prostate cancer), pancreatic cancer (e.g., pancreatic duct cancer), gastric cancer (e.g., papillary adenocarcinoma, mucinous adenocarcinoma, and adenosquamous carcinoma), lung cancer (e.g., non-small-cell lung cancer, small-cell lung cancer, and malignant mesothelioma), colon cancer (e.g., gastrointestinal stromal tumor), rectal cancer (e.g., gastrointestinal stromal tumor), colorectal cancer (e.g., familial colorectal cancer, hereditary nonpolyposis colorectal cancer, and gastrointestinal stromal tumor), small intestinal cancer (e.g., gastrointestinal stromal tumor), esophageal cancer, duodenal cancer, tongue cancer, pharyngeal cancer (e.g., nasopharyngeal cancer, oropharynx cancer, and hypopharyngeal cancer), salivary gland cancer, brain tumor (e.g., pineal astrocytoma, pilocytic astrocytoma, diffuse astrocytoma, and anaplastic astrocytoma), neurilemmoma, liver cancer (e.g., primary liver cancer and extrahepatic bile duct cancer), renal cancer (e.g., renal cell cancer and transitional cell cancer of the renal pelvis and ureter), bile duct cancer, endometrial cancer, cervical cancer, uterine sarcoma, ovarian cancer (e.g., epithelial ovarian cancer, extragonadal germ cell tumor, ovarian germ cell tumor, and ovarian low-malignant potential tumor), bladder cancer, urethral cancer, skin cancer (e.g., intraocular (ocular) melanoma and Merkel cell carcinoma), hemangioma, malignant lymphoma (e.g., non-Hodgkin's lymphoma and Hodgkin's lymphoma), malignant melanoma, thyroid cancer (e.g., medullary thyroid cancer), parathyroid cancer, nasal cancer, paranasal cancer, myeloma (e.g., multiple myeloma), bone tumor (e.g., osteosarcoma, Ewing's tumor, and soft-tissue sarcoma), myelodysplastic tumor, myeloproliferative tumor, hemangiofibroma, retinal sarcoma, penile cancer, testicular tumor, pediatric solid cancer (e.g., Wilms tumor and pediatric renal tumor), Kaposi sarcoma, Kaposi sarcoma caused by AIDS, tumor of maxillary sinus, fibrous histiocytoma, leiomyosarcoma, rhabdomyosarcoma, leukemia (e.g., acute myelogenous leukemia, chronic myelogenous leukemia, and acute lymphoblastic leukemia), and the like. Among these, the type of cancer particularly preferred as the target to which the antitumor composition, kit, or prevention or treatment method of the present disclosure is applied includes malignant lymphoma, leukemia, myeloma, breast cancer, gastric cancer, pancreatic cancer, lung cancer, ovarian cancer, and the like.

In the present specification, the term "comprising" includes "consisting essentially of" and "consisting of."

The various characteristics (properties, structures, functions, etc.) that are explained in the above embodiments can be combined in any manner to specify the subject matter encompassed in the present disclosure.

EXAMPLES

The subject matter encompassed in the present disclosure is described in more detail below. However, the subject matter is not limited to the following Examples.

According to the method described in the Examples (in particular, Example 24) of WO2012/046825, N-{6-[2-methyl-4-(methylamino)phenoxy]pyridin-3-yl}-4-(trifluoromethyl)benzamide hydrochloride (white powder) was prepared. The N-{6-[2-methyl-4-(methylamino)phenoxy]pyridin-3-yl}-4-(trifluoromethyl)benzamide hydrochloride is also referred to as compound A below. The obtained white powder of compound A was used as "compound A bulk powder" in the following examinations.

[In Vitro Growth Inhibition Test]

Example 1: Combination Effect of Compound A and Bendamustine on Human Follicular Lymphoma Cell Line DOHH-2

1) Test Substance

The compound A bulk powder was used. Bendamustine used was purchased from Tokyo Chemical Industry Co., Ltd.

2) Cell Culture

DOHH-2 cells were purchased from Deutsche Sammlung von Mikroorganismen und Zellkulturen GmbH (DSMZ). The cells were cultured in RPMI-1640 medium supplemented with 10% inactivated (treated at 56° C. for 30 minutes) fetal bovine serum, penicillin, and streptomycin under the conditions of 37° C. and 5% $CO_2$. The cells were collected and resuspended by a conventional method, and seeded on a 96-well plate at 1000 cells/well. The number of seeded cells was defined as the number of cells from which the linearity of the cell growth curve was obtained until the 6th day.

3) Drug Addition

After culturing the cells for 24 hours at 37° C. and 5% $CO_2$, media containing various concentrations of compound A or various concentrations of the antitumor agent used in combination were added. After stirring the plate, the cells were cultured at 37° C. and 5% $CO_2$ for 120 hours.

4) Cell Growth Inhibition Test

A cell growth inhibition test was performed using the CellTiter-Fluor Cell Viability Assay (Promega). Specifically, CellTiter-Fluor reagent was added to each well to be measured, followed by incubation. Then, the fluorescence intensity was measured with a fluorescence microplate reader at an excitation wavelength of 400 nm and a fluorescence wavelength of 505 nm.

5) Calculation of Cell Viability

A cell-free blank value was subtracted from the measured value of each well, and the ratio relative to the drug-free control was calculated and defined as cell viability. The $IC_{50}$ value described below was determined using the cell viability.

6) Isobologram Analysis

The combination effect of compound A and the combined antitumor agent (bendamustine) was evaluated using the isobologram method. Specifically, the evaluation was performed as follows.

The $IC_{50}$ value of compound A in each concentration of the antitumor agent (test compound concentration required to inhibit cell proliferation by 50% relative to the untreated group) was determined. The fractional inhibitory concentration (FIC) of the antitumor agent was determined by dividing each concentration of the antitumor agent by the $IC_{50}$ value of the antitumor agent alone. The FIC of compound A was determined by dividing the $IC_{50}$ value of compound A at that time by the $IC_{50}$ value of compound A alone. The $IC_{50}$ value of the antitumor agent in each concentration of compound A was determined in the same manner. The FIC of compound A was determined by dividing each concentration of compound A by the $IC_{50}$ value of compound A alone. The FIC of the antitumor agent was determined by dividing the $IC_{50}$ value of the antitumor agent at that time by the $IC_{50}$ value of the antitumor agent alone. The total FIC value of each combination was defined as the CI value of each combination. The CI average value and the 95% confidence interval were calculated. Table 1 shows the details of the calculation.

TABLE 1

Antitumor agent bendamustine, cancer: follicular lymphoma, cell line: DOHH-2, number of seeded cells: 1000 cells/well

| Bendamustine (nM) | IC50 value of compound A in each concentration of bendamustine (nM) | Bendamustine FIC | Compound A FIC | CI |
| --- | --- | --- | --- | --- |
| 0 | 381.08 | 0 | 1 | — |
| 1250 | 226.68 | 0.127 | 0.595 | 0.721 |
| 2500 | 98.50 | 0.253 | 0.258 | 0.512 |
| 5000 | 46.73 | 0.506 | 0.123 | 0.629 |

| Compound A (nM) | IC50 value of bendamustine in each concentration of compound A (nM) | Compound A (FIC) | Bendamustine FIC | CI |
| --- | --- | --- | --- | --- |
| 0 | 9872.83 | 0 | 1 | — |
| 39.1 | 5585.72 | 0.103 | 0.566 | 0.668 |
| 78.1 | 2957.25 | 0.205 | 0.300 | 0.505 |
| 156.3 | 1500.73 | 0.410 | 0.152 | 0.562 |
| 312.5 | 40.54 | 0.820 | 0.004 | 0.824 |

Further, FIG. 1 shows a graph plotting the FIC of each drug (compound A and bendamustine). In the isobologram, plots located at the upper right, almost on the line, or at the lower left, from the straight line connecting the points where the FIC of each drug is 1, mean that an antagonistic, additive, or synergistic effect is exhibited, respectively. The plots shown in FIG. 1 were located at the lower left of the straight line, indicating that the combined use of compound A and bendamustine showed a synergistic effect on the cell growth inhibition of DOHH-2.

Example 2: Combination Effect of Compound A and Bendamustine on Human Breast Cancer Cell Line MDA-MB-231

1) Test Substance

The compound A bulk powder was used. Bendamustine used was purchased from Tokyo Chemical Industry Co., Ltd.

2) Cell Growth Inhibition Test

MDA-MB-231 cells were purchased from the American Type Culture Collection (ATCC).

The cell culture, drug addition, cell growth inhibition test, calculation of cell viability, and isobologram analysis were performed in the same manner as in Example 1 except that the number of seeded cells was 2000 cells/well. FIG. 2 shows the isobologram analysis results. The plots shown in FIG. 2 were located at the lower left of the straight line, indicating that the combined use of compound A and bendamustine showed a synergistic effect on the cell growth inhibition of MDA-MB-231.

Example 3: Combination Effect of Compound A and Decitabine on Human Acute Myelogenous Leukemia (AML) Cell Line CMK-86

1) Test Substance

The compound A bulk powder was used. Decitabine used was purchased from Tokyo Chemical Industry Co., Ltd.

2) Cell Growth Inhibition Test

CMK-86 cells were purchased from the Health Science Research Resources Bank.

The cell culture, drug addition, cell growth inhibition test, calculation of cell viability, and isobologram analysis were performed in the same manner as in Example 1 except that the number of seeded cells was 12000 cells/well. FIG. 3 shows the isobologram analysis results. The plots shown in FIG. 3 were located at the lower left of the straight line, indicating that the combined use of compound A and decitabine showed a synergistic effect on the cell growth inhibition of CMK-86.

Example 4: Combination Effect of Compound A and Busulfan on Human Acute Myelogenous Leukemia (AML) Cell Line MV-4-11

1) Test Substance

The compound A bulk powder was used. Busulfan used was purchased from Wako Pure Chemical Industries, Ltd.

2) Cell Growth Inhibition Test

MV-4-11 cells were purchased from ATCC.

The cell culture, drug addition, cell growth inhibition test, calculation of cell viability, and isobologram analysis were performed in the same manner as in Example 1 except that the number of seeded cells was 8000 cells/well. FIG. 4 shows the isobologram analysis results. The plots shown in FIG. 4 were located at the lower left of the straight line, indicating that the combined use of compound A and busulfan showed a synergistic effect on the cell growth inhibition of MV-4-11.

Example 5: Combination Effect of Compound A and Lomustine on Human Chronic Myelogenous Leukemia (CML) Cell Line K562

1) Test Substance

The compound A bulk powder was used. Lomustine used was purchased from Tokyo Chemical Industry Co., Ltd.

2) Cell Growth Inhibition Test

K562 cells were purchased from the Health Science Research Resources Bank.

The cell culture, drug addition, cell growth inhibition test, calculation of cell viability, and isobologram analysis were performed in the same manner as in Example 1. FIG. 5 shows the isobologram analysis results. The plots shown in FIG. 5 were located at the lower left of the straight line, indicating that the combined use of compound A and lomustine showed a synergistic effect on the cell growth inhibition of K562.

Example 6: Combination Effect of Compound A and Thiotepa on Human Lung Cancer Cell Line A549

1) Test Substance

The compound A bulk powder was used. Thiotepa used was purchased from Sigma-Aldrich.

2) Cell Growth Inhibition Test

A549 cells were purchased from the Health Science Research Resources Bank.

The cell culture, drug addition, cell growth inhibition test, calculation of cell viability, and isobologram analysis were performed in the same manner as in Example 1. FIG. 6 shows the isobologram analysis results. The plots shown in FIG. 6 were located at the lower left of the straight line, indicating that the combined use of compound A and thiotepa showed a synergistic effect on the cell growth inhibition of A549.

Example 7: Combination Effect of Compound A and Lomustine on Human Pancreatic Cancer Cell Line BxPC-3

1) Test Substance

Lomustine used was purchased from Tokyo Chemical Industry Co., Ltd. The compound A bulk powder was used.

2) Cell Growth Inhibition Test

BxPC-3 cells were purchased from ATCC.

The cell culture, drug addition, cell growth inhibition test, calculation of cell viability, and isobologram analysis were performed in the same manner as in Example 1. FIG. 7 shows the isobologram analysis results. The plots shown in FIG. 7 were located at the lower left of the straight line, indicating that the combined use of compound A and lomustine showed a synergistic effect on the cell growth inhibition of BxPC-3.

Example 8: Combination Effect of Compound A and Melphalan on Human Acute Myelogenous Leukemia (AML) Cell Line KG-1

1) Test Substance

The compound A bulk powder was used. Melphalan used was purchased from Sigma-Aldrich.

2) Medium and Cell Passage

KG-1 cells were purchased from the Health Science Research Resources Bank.

The cell culture, drug addition, cell growth inhibition test, calculation of cell viability, and isobologram analysis were performed in the same manner as in Example 1 except that the number of seeded cells was 8000 cells/well. FIG. 8 shows the isobologram analysis results. The plots shown in FIG. 8 were located at the lower left of the straight line, indicating that the combined use of compound A and melphalan showed a synergistic effect on the cell growth inhibition of KG-1.

Example 9: Combination Effect of Compound A and Lomustine on Human Diffuse Large B-Cell Lymphoma (DLBCL) Cell Line U2932

1) Test Substance

The compound A bulk powder was used. Lomustine used was purchased from Tokyo Chemical Industry Co., Ltd.

2) Cell Growth Inhibition Test

U2932 cells were purchased from DSMZ.

The cell culture, drug addition, cell growth inhibition test, calculation of cell viability, and isobologram analysis were performed in the same manner as in Example 1 except that the number of seeded cells was 2000 cells/well. FIG. 9 shows the isobologram analysis results. The plots shown in FIG. 9 were located at the lower left of the straight line, indicating that the combined use of compound A and lomustine showed a synergistic effect on the cell growth inhibition of U2932.

Example 10: Combination Effect of Compound A and Melphalan on Human Diffuse Large B-Cell Lymphoma (DLBCL) Cell Line U2932

1) Test Substance

The compound A bulk powder was used. Melphalan used was purchased from Sigma-Aldrich.

2) Cell Growth Inhibition Test

U2932 cells were purchased from DSMZ.

The cell culture, drug addition, cell growth inhibition test, calculation of cell viability, and isobologram analysis were performed in the same manner as in Example 1 except that the number of seeded cells was 2000 cells/well. FIG. 10 shows the isobologram analysis results. The plots shown in FIG. 10 were located at the lower left of the straight line, indicating that the combined use of compound A and melphalan showed a synergistic effect on the cell growth inhibition of U2932.

Example 11: Combination Effect of Compound A and Melphalan on Human Acute Myelogenous Leukemia (AML) Cell Line MV-4-11

1) Test Substance

The compound A bulk powder was used. Melphalan used was purchased from Sigma-Aldrich.

2) Cell Growth Inhibition Test

MV-4-11 cells were purchased from ATCC.

The cell culture, drug addition, cell growth inhibition test, calculation of cell viability, and isobologram analysis were performed in the same manner as in Example 1 except that the number of seeded cells was 8000 cells/well. FIG. 11 shows the isobologram analysis results. The plots shown in FIG. 11 were located at the lower left of the straight line, indicating that the combined use of compound A and melphalan showed a synergistic effect on the cell growth inhibition of MV-4-11.

Example 12: Combination Effect of Compound A and Lomustine on Human Gastric Cancer Cell Line MKN45

1) Test Substance

The compound A bulk powder was used. Lomustine used was purchased from Tokyo Chemical Industry Co., Ltd.

2) Cell Growth Inhibition Test

MKN 45 cells were purchased from the Health Science Research Resources Bank.

The cell culture, drug addition, cell growth inhibition test, calculation of cell viability, and isobologram analysis were performed in the same manner as in Example 1. FIG. 12 shows the isobologram analysis results. The plots shown in FIG. 12 were located at the lower left of the straight line, indicating that the combined use of compound A and lomustine showed a synergistic effect on the cell growth inhibition of MKN 45.

Example 13: Combination Effect of Compound A and Decitabine on Human Acute Myelogenous Leukemia (AML) Cell Line MV-4-11

1) Test Substance

The compound A bulk powder was used. Decitabine used was purchased from Tokyo Chemical Industry Co., Ltd.

2) Cell Growth Inhibition Test

MV-4-11 cells were purchased from ATCC.

The cell culture, drug addition, cell growth inhibition test, calculation of cell viability, and isobologram analysis were performed in the same manner as in Example 1 except that the number of seeded cells was 8000 cells/well. FIG. 13 shows the isobologram analysis results. The plots shown in FIG. 13 were located at the lower left of the straight line, indicating that the combined use of compound A and decitabine showed a synergistic effect on the cell growth inhibition of MV-4-11.

Example 14: Combination Effect of Compound A and Decitabine on Human Acute Myelogenous Leukemia (AML) Cell Line OCI-AML2

1) Test Substance

The compound A bulk powder was used. Decitabine used was purchased from Tokyo Chemical Industry Co., Ltd.

2) Cell Growth Inhibition Test OCI-AML2 cells were purchased from DSMZ.

The cell culture, drug addition, cell growth inhibition test, calculation of cell viability, and isobologram analysis were performed in the same manner as in Example 1 except that the number of seeded cells was 4000 cells/well. FIG. 14 shows the isobologram analysis results. The plots shown in FIG. 14 were located at the lower left of the straight line, indicating that the combined use of compound A and decitabine showed a synergistic effect on the cell growth inhibition of OCI-AML2.

Example 15: Combination Effect of Compound A and Cytarabine on Human Acute Myelogenous Leukemia (AML) Cell Line MV-4-11

1) Test Substance

The compound A bulk powder was used. Cytarabine used was purchased from Wako Pure Chemical Industries, Ltd.

2) Cell Growth Inhibition Test

MV-4-11 cells were purchased from ATCC.

The cell culture, drug addition, cell growth inhibition test, calculation of cell viability, and isobologram analysis were performed in the same manner as in Example 1 except that the number of seeded cells was 8000 cells/well. FIG. 15 shows the isobologram analysis results. The plots shown in FIG. 15 were located at the lower left of the straight line, indicating that the combined use of compound A and cytarabine showed a synergistic effect on the cell growth inhibition of MV-4-11.

Example 16: Combination Effect of Compound A and Bendamustine on Human Breast Cancer Cell Line BT-474

1) Test Substance

The compound A bulk powder was used. Bendamustine used was purchased from Tokyo Chemical Industry Co., Ltd.

2) Cell Growth Inhibition Test

BT-474 cells were purchased from ATCC.

The cell culture, drug addition, cell growth inhibition test, calculation of cell viability, and isobologram analysis were performed in the same manner as in Example 1 except that the number of seeded cells was 8000 cells/well. FIG. 16 shows the isobologram analysis results. The plots shown in FIG. 16 were located at the lower left of the straight line, indicating that the combined use of compound A and bendamustine showed a synergistic effect on the cell growth inhibition of BT-474.

Example 17: Combination Effect of Compound A and Melphalan on Human Multiple Myeloma Cell Line RPMI 8226

1) Test Substance

The compound A bulk powder was used. Melphalan used was purchased from Sigma-Aldrich.

2) Cell Growth Inhibition Test

RPMI 8226 cells were purchased from ATCC.

The cell culture, drug addition, cell growth inhibition test, calculation of cell viability, and isobologram analysis were performed in the same manner as in Example 1 except that the number of seeded cells was 4000 cells/well. FIG. 17 shows the isobologram analysis results. The plots shown in FIG. 17 were located at the lower left of the straight line, indicating that the combined use of compound A and melphalan showed a synergistic effect on the cell growth inhibition of RPMI 8226.

Example 18: Combination Effect of Compound A and Venetoclax on Human Acute Myelogenous Leukemia (AML) Cell Line KG-1

1) Test Substance

The compound A bulk powder was used. Venetoclax used was purchased from LC Laboratories.

2) Cell Growth Inhibition Test

KG-1 cells were purchased from the Health Science Research Resources Bank.

The cell culture, drug addition, cell growth inhibition test, calculation of cell viability, and isobologram analysis were performed in the same manner as in Example 1 except that the number of seeded cells was 8000 cells/well. FIG. 18 shows the isobologram analysis results. The plots shown in FIG. 18 were located at the lower left of the straight line, indicating that the combined use of compound A and venetoclax showed a synergistic effect on the cell growth inhibition of KG-1.

Example 19: Combination Effect of Compound A and Ranimustine on Human Chronic Myelogenous Leukemia (CML) Cell Line K562

1) Test Substance

The compound A bulk powder was used. Ranimustine used was purchased from Toronto Research Chemicals.

2) Cell Growth Inhibition Test

K562 cells were purchased from the Health Science Research Resources Bank.

The cell culture, drug addition, cell growth inhibition test, calculation of cell viability, and isobologram analysis were performed in the same manner as in Example 1. FIG. 19 shows the isobologram analysis results. The plots shown in FIG. 19 were located at the lower left of the straight line, indicating that the combined use of compound A and ranimustine showed a synergistic effect on the cell growth inhibition of K562.

Example 20: Combination Effect of Compound A and Thiotepa on Human Ovarian Cancer Cell Line SK-OV-3

1) Test Substance

The compound A bulk powder was used. Thiotepa used was purchased from Sigma-Aldrich.

2) Cell Growth Inhibition Test

SK-OV-3 cells were purchased from ATCC.

The cell culture, drug addition, cell growth inhibition test, calculation of cell viability, and isobologram analysis were performed in the same manner as in Example 1. FIG. 20 shows the isobologram analysis results. The plots shown in FIG. 20 were located at the lower left of the straight line, indicating that the combined use of compound A and thiotepa showed a synergistic effect on the cell growth inhibition of SK-OV-3.

Example 21: Combination Effect of Compound A and Ibrutinib on Human Acute Myelogenous Leukemia (AML) Cell Line MV-4-11

1) Test Substance

The compound A bulk powder was used. Ibrutinib used was purchased from MedChem Express.

2) Cell Growth Inhibition Test

MV-4-11 cells were purchased from ATCC. The cell culture, drug addition, cell growth inhibition test, calculation of cell viability, and isobologram analysis were performed in the same manner as in Example 1 except that the number of seeded cells was 8000 cells/well. FIG. 21 shows the isobologram analysis results.

The plots shown in FIG. 21 were located at the lower left of the straight line, indicating that the combined use of compound A and ibrutinib showed a synergistic effect on the cell growth inhibition of MV-4-11.

Example 22: Combination Effect of Compound A and Decitabine on Human Myelodysplastic Syndrome Cell Line SKM-1

1) Test Substance

The compound A bulk powder was used. Decitabine used was purchased from Tokyo Chemical Industry Co., Ltd.

2) Cell Growth Inhibition Test

SKM-1 cells were purchased from the National Institutes of Biomedical Innovation, Health and Nutrition, JCRB Cell Bank (JCRB). The cell culture, drug addition, cell growth inhibition test, calculation of cell viability, and isobologram analysis were performed in the same manner as in Example 1 except that the number of seeded cells was 8000 cells/well. FIG. 22 shows the isobologram analysis results.

The plots shown in FIG. 22 were located at the lower left of the straight line, indicating that the combined use of compound A and decitabine showed a synergistic effect on the cell growth inhibition of SKM-1.

Example 23: Combination Effect of Compound A and Erlotinib on Human Lung Cancer Cell Line A549

1) Test Substance

The compound A bulk powder was used. Erlotinib used was purchased from Wako Pure Chemical Industries, Ltd.

2) Cell Growth Inhibition Test

A549 cells were purchased from the Health Science Research Resources Bank. The cell culture, drug addition, cell growth inhibition test, calculation of cell viability, and isobologram analysis were performed in the same manner as in Example 1 except that the number of seeded cells was 1000 cells/well. FIG. 23 shows the isobologram analysis results.

The plots shown in FIG. 23 were located at the lower left of the straight line, indicating that the combined use of compound A and erlotinib showed a synergistic effect on the cell growth inhibition of A549.

Example 24: Combination Effect of Compound A and Gefitinib on Human Lung Cancer Cell Line A549

1) Test Substance

The compound A bulk powder was used. Gefitinib used was purchased from Wako Pure Chemical Industries, Ltd.

2) Cell Growth Inhibition Test

A549 cells were purchased from the Health Science Research Resources Bank. The cell culture, drug addition, cell growth inhibition test, calculation of cell viability, and isobologram analysis were performed in the same manner as in Example 1 except that the number of seeded cells was 1000 cells/well. FIG. 24 shows the isobologram analysis results.

The plots shown in FIG. 24 were located at the lower left of the straight line, indicating that the combined use of compound A and gefitinib showed a synergistic effect on the cell growth inhibition of A549.

Example 25: Combination Effect of Compound A and Gefitinib on Human Lung Cancer Cell Line HCC 827

1) Test Substance

The compound A bulk powder was used. Gefitinib used was purchased from Wako Pure Chemical Industries, Ltd.

2) Cell Growth Inhibition Test

HCC 827 cells were purchased from ATCC. The cell culture, drug addition, cell growth inhibition test, calculation of cell viability, and isobologram analysis were performed in the same manner as in Example 1 except that the number of seeded cells was 4000 cells/well. FIG. 25 shows the isobologram analysis results.

The plots shown in FIG. 25 were located at the lower left of the straight line, indicating that the combined use of compound A and gefitinib showed a synergistic effect on the cell growth inhibition of HCC 827.

Example 26: Combination Effect of Compound A and Imatinib on Human Chronic Myelogenous Leukemia (CML) Cell Line K562

1) Test Substance

The compound A bulk powder was used. Imatinib used was purchased from Wako Pure Chemical Industries, Ltd.

2) Cell Growth Inhibition Test

K562 cells were purchased from the Health Science Research Resources Bank. The cell culture, drug addition, cell growth inhibition test, calculation of cell viability, and isobologram analysis were performed in the same manner as in Example 1 except that the number of seeded cells was 1000 cells/well. FIG. 26 shows the isobologram analysis results.

The plots shown in FIG. 26 were located at the lower left of the straight line, indicating that the combined use of compound A and imatinib showed a synergistic effect on the cell growth inhibition of K562.

Example 27: Combination Effect of Compound A and Axitinib on Human Renal Cancer Cell Line ACHN 1) Test Substance The compound A bulk powder was used. Axitinib used was purchased from Selleck Biotech.

2) Cell Growth Inhibition Test

ACHN cells were obtained from Otsuka Pharmaceutical TRC. The cell culture, drug addition, cell growth inhibition test, calculation of cell viability, and isobologram analysis were performed in the same manner as in Example 1 except that the number of seeded cells was 8000 cells/well. FIG. 27 shows the isobologram analysis results.

The plots shown in FIG. 27 were located at the lower left of the straight line, indicating that the combined use of compound A and axitinib showed a synergistic effect on the cell growth inhibition of ACHN.

Example 28: Combination Effect of Compound A and Lapatinib on Human Breast Cancer Cell Line MDA-MB-453

1) Test Substance

The compound A bulk powder was used. Lapatinib used was purchased from LC Laboratories.

2) Cell Growth Inhibition Test

MDA-MB-453 cells were purchased from ATCC. The cell culture, drug addition, cell growth inhibition test, calculation of cell viability, and isobologram analysis were performed in the same manner as in Example 1 except that the number of seeded cells was 8000 cells/well. FIG. 28 shows the isobologram analysis results.

The plots shown in FIG. 28 were located at the lower left of the straight line, indicating that the combined use of compound A and lapatinib showed a synergistic effect on the cell growth inhibition of MDA-MB-453.

Example 29: Combination Effect of Compound A and Lenvatinib on Human Hepatoma Cell Line Hep G2

1) Test Substance

The compound A bulk powder was used. Lenvatinib used was purchased from Funakoshi Co., Ltd.

2) Cell Growth Inhibition Test

Hep G2 cells were purchased from ATCC. The cell culture, drug addition, cell growth inhibition test, calculation of cell viability, and isobologram analysis were performed in the same manner as in Example 1 except that the number of seeded cells was 2000 cells/well. FIG. 29 shows the isobologram analysis results.

The plots shown in FIG. 29 were located at the lower left of the straight line, indicating that the combined use of compound A and lenvatinib showed a synergistic effect on the cell growth inhibition of Hep G2.

Example 30: Combination Effect of Compound A and Lapatinib on Human Breast Cancer Cell Line SK-BR-3

1) Test Substance

The compound A bulk powder was used. Lapatinib used was purchased from LC Laboratories.

2) Cell Growth Inhibition Test

SK-BR-3 cells were purchased from ATCC. The cell culture, drug addition, cell growth inhibition test, calculation of cell viability, and isobologram analysis were performed in the same manner as in Example 1 except that the number of seeded cells was 4000 cells/well. FIG. 30 shows the isobologram analysis results.

The plots shown in FIG. 30 were located at the lower left of the straight line, indicating that the combined use of compound A and lapatinib showed a synergistic effect on the cell growth inhibition of SK-BR-3.

Example 31: Combination Effect of Compound A and Afatinib on Human Lung Cancer Cell Line A549

1) Test Substance

The compound A bulk powder was used. Afatinib used was purchased from Tokyo Chemical Industry Co., Ltd.

2) Cell Growth Inhibition Test

A549 cells were purchased from the Health Science Research Resources Bank. The cell culture, drug addition, cell growth inhibition test, calculation of cell viability, and isobologram analysis were performed in the same manner as in Example 1 except that the number of seeded cells was 1000 cells/well. FIG. 31 shows the isobologram analysis results.

The plots shown in FIG. 31 were located at the lower left of the straight line, indicating that the combined use of compound A and afatinib showed a synergistic effect on the cell growth inhibition of A549.

Example 32: Combination Effect of Compound A and Gilteritinib on Human Acute Myelogenous Leukemia (AML) Cell Line MV-4-11

1) Test Substance

The compound A bulk powder was used. Gilteritinib used was purchased from Cayman Chemical Company.

2) Cell Growth Inhibition Test

MV-4-11 cells were purchased from ATCC. The cell culture, drug addition, cell growth inhibition test, calculation of cell viability, and isobologram analysis were performed in the same manner as in Example 1 except that the number of seeded cells was 8000 cells/well. FIG. 32 shows the isobologram analysis results.

The plots shown in FIG. 32 were located at the lower left of the straight line, indicating that the combined use of compound A and gilteritinib showed a synergistic effect on the cell growth inhibition of MV-4-11.

Example 33: Combination Effect of Compound A and 5-FU on Human Head and Neck (Pharyngeal) Cancer Cell Line FaDu 1) Test Substance The compound A bulk powder was used. 5-FU used was purchased from Sigma-Aldrich.

2) Cell Growth Inhibition Test

FaDu cells were purchased from ATCC. The cell culture, drug addition, cell growth inhibition test, calculation of cell viability, and isobologram analysis were performed in the same manner as in Example 1 except that the number of seeded cells was 1000 cells/well. FIG. 33 shows the isobologram analysis results.

The plots shown in FIG. 33 were located at the lower left of the straight line, indicating that the combined use of compound A and 5-FU showed a synergistic effect on the cell growth inhibition of FaDu.

Comparative Example 1: Combination Effect of Compound A and Vincristine on Human Diffuse Large B-Cell Lymphoma Cell Line OCI-Ly18

1) Test Substance

The compound A bulk powder was used. Vincristine used was purchased from Wako Pure Chemical Industries, Ltd.

2) Cell Growth Inhibition Test

OCI-Ly18 cells were purchased from DSMZ. The cell culture, drug addition, cell growth inhibition test, calculation of cell viability, and isobologram analysis were performed in the same manner as in Example 1 except that the number of seeded cells was 16000 cells/well. FIG. 34 shows the isobologram analysis results. The plots shown in FIG. 34 were located almost on the straight line, indicating that the combined use of compound A and vincristine showed only an additive effect on the cell growth inhibition of OCI-Ly18.

Comparative Example 2: Combination Effect of Compound A and Docetaxel on Human Breast Cancer Cell Line BT-474

1) Test Substance

The compound A bulk powder was used. Docetaxel used was purchased from Wako Pure Chemical Industries, Ltd.

2) Cell Growth Inhibition Test

BT-474 cells were purchased from ATCC. The cell culture, drug addition, cell growth inhibition test, calculation of cell viability, and isobologram analysis were performed in the same manner as in Example 1 except that the number of seeded cells was 8000 cells/well. FIG. 35 shows the isobologram analysis results.

The plots shown in FIG. 35 were located almost on the straight line, indicating that the combined use of compound A and docetaxel showed only an additive effect on the cell growth inhibition of BT-474.

Example 34: Combination Effect of Compound A and Bendamustine on Human Diffuse Large B-Cell Lymphoma (DLBCL) Cell Line OCI-Ly7

1) Test Substance

The compound A bulk powder was used. Bendamustine used was purchased from Tokyo Chemical Industry Co., Ltd.

2) Cell Growth Inhibition Test

OCI-Ly7 cells were purchased from DSMZ. The cell culture, drug addition, cell growth inhibition test, and calculation of cell viability were performed in the same manner as in Example 1 except that the number of seeded cells was 8000 cells/well. Table 2 shows the results.

TABLE 2

Antitumor agent bendsmustine, cancer: diffuse large B-cell lymphoma (DLBCL), cell line: OCI-Ly7, number of seeded cells: 8000 cells/well

| Compound A (nM) | Bendamustine (nM) | Cell viability |
|---|---|---|
| 0 | 0 | 1.00 |
| 0.25 | 0 | 0.79 |
| 0.5 | 0 | 0.76 |
| 1 | 0 | 0.61 |
| 2 | 0 | 0.50 |
| 0 | 1.25 | 0.93 |
| 0 | 2.5 | 0.87 |
| 0 | 5 | 0.66 |
| 0 | 10 | 0.29 |
| 0.25 | 1.25 | 0.62 |
| 0.5 | 2.5 | 0.54 |
| 1 | 5 | 0.35 |
| 2 | 10 | 0.16 |

3) Statistical Analysis

The combination index (CI) and 95% confidence interval were calculated using SAS software Release 9.3 (SAS Institute JAPAN).

The CI was 0.67, and the 95% confidence interval was 0.37 to 0.96.

A CI of greater than 1, equal to 1, or less than 1 means that an antagonistic, additive, or synergistic effect is exhibited, respectively. Therefore, it was found that the combined use of compound A and bendamustine showed a synergistic effect on OCI-Ly7 cell growth inhibition.

Example 35: Combination Effect of Compound A and Bendamustine on Human Mantle Cell Lymphoma Cell Line REC-1

1) Test Substance

The compound A bulk powder was used. Bendamustine used was purchased from Tokyo Chemical Industry Co., Ltd.

2) Cell Growth Inhibition Test

REC-1 cells were purchased from DSMZ.

The cell culture, drug addition, cell growth inhibition test, and calculation of cell viability were performed in the same manner as in Example 1 except that the number of seeded cells was 8000 cells/well. Using the obtained results, the combination index (CI) and 95% confidence interval were calculated in the same manner as in Example 34.

The CI was 0.65, and the 95% confidence interval was 0.34 to 0.96. Therefore, it was found that the combined use of compound A and bendamustine showed a synergistic effect on REC-1 cell growth inhibition.

[In Vivo Antitmanor Effect Test]

Example 36: Combination Effect of Compound A and Cyclophosphamide on Human Diffuse Large B-Cell Lymphoma Cell Line OCI-Ly7

1) Test Substance

The compound A bulk powder was used. Cyclophosphamide (Endoxan for Injection (trademark) 100 mg) used was purchased from Shionogi & Co., Ltd.

2) Preparation of Test Substance

Compound A was suspended in a 1% hypromellose solution to prepare a 10 mg/mL (100 mg/kg administration solution) test substance suspension. The test substance suspension was diluted with a 1% hypromellose solution to prepare 3 mg/mL (30 mg/kg administration solution) and 1 mg/mL (10 mg/kg administration solution) test substance suspensions. Further, 100 mg of commercially available Endoxan for Injection was dissolved in 20 mL of saline, and a 5 mg/mL solution (50 mg/kg administration solution) was prepared at the time of use. This solution was used as cyclophosphamide.

3) Cells

OCI-Ly7 was obtained from DSMZ. The cells were cultured in RPMI 1640 medium supplemented with 10% inactivated (treated at 56° C. for 30 minutes) fetal bovine serum under the conditions of 37° C. and 5% $CO_2$. The collected cells were suspended in serum-free RPMI 1640 medium at $1.5 \times 10^8$ cells/mL.

4) Animal 5-week-old female SCID mice (C.B-17/Icr-scid/scid Jcl, produced by CLEA Japan, Inc.) were used. The female SCID mice were bred with a standard diet and drinking water under specific pathogen-free (SPF) conditions throughout the examination period. The cell suspension was inoculated at $3 \times 10^7$ cells/body into the subcutaneous space of the right axillary region of the 6-week-old SCID mice. Using the tumor volume as an index, grouping was performed by a stratified random sampling method using SAS software R9.3 (SAS Institute Japan).

5) Administration and Measurement

The administration was started on the next day of the grouping (Day 2). Compound A was orally administered once a day for 14 consecutive days, and cyclophosphamide was administered intraperitoneally once every 3 or 4 days, 4 times in total. In order to match with the combination group, a solvent of each drug was administered to the control group, and a solvent of the combined drug was administered to the monotherapy group, as in the combination therapy group. All of the animals received oral administration for 14 consecutive days and intraperitoneal administration once every 3 or 4 days (4 times in total). Each group (N=8) was treated as follows.

(1) Control (solvent control) group: 1% hypromellose solution, saline
(2) Compound A (10 mg/kg) treated group: 10 mg/kg of compound A (oral administration once a day for 14 consecutive days)
(3) Compound A (30 mg/kg) treated group: 30 mg/kg of compound A (oral administration once a day for 14 consecutive days)
(4) Compound A (100 mg/kg) treated group: 100 mg/kg of compound A (oral administration once a day for 14 consecutive days)
(5) Cyclophosphamide (50 mg/kg) treated group: 50 mg/kg of cyclophosphamide (intraperitoneal administration on Days 2, 5, 9, and 12)
(6) Combination group 1: 10 mg/kg of compound A (oral administration once a day for 14 consecutive days)+50 mg/kg of cyclophosphamide (intraperitoneal administration on Days 2, 5, 9, and 12)

(7) Combination group 2: 30 mg/kg of compound A (oral administration once a day for 14 consecutive days)+50 mg/kg of cyclophosphamide (intraperitoneal administration on Days 2, 5, 9, and 12)

(8) Combination group 3: 100 mg/kg of compound A (oral administration once a day for 14 consecutive days)+50 mg/kg of cyclophosphamide (intraperitoneal administration on Days 2, 5, 9, and 12)

The body weight and the tumor diameter were measured over time using an electronic balance and electronic digital caliper.

The tumor volume was calculated from tumor diameters by the following formula: (Long diameter×[Short diameter]$^2$×0.5). Using the calculated tumor volume value, the relative tumor volume (ratio of the tumor volume on the day of measurement to the baseline tumor volume on Day 1) was calculated. The time for relative tumor volume of each animal to reach 1600% from the grouping day (Day 1) was estimated using data on adjacent measurement day for relative tumor volume to reach 1600%. The tumor growth delay (TGD) was calculated as the difference in the median time for relative tumor volume of the treated and control groups to reach 1600%. Further, the tumor growth delay rate (% TGD) was calculated according to the following formula:

% TGD={$(T-C)/C$}×100,

Where:
T: the median time for relative tumor volume of treated groups to reach 1600%
C: the median time for relative tumor volume of the control group to reach 1600%

6) Statistical Analysis

The influence of compound A monotherapy on tumor growth delay was evaluated using two-tailed Steel test based on the time for relative tumor volume of each animal to reach 1600% between the control group (group 1) and each compound A monotherapy group (groups 2, 3, and 4).

The influence of cyclophosphamide monotherapy on tumor growth delay was evaluated using two-tailed Wilcoxon rank-sum test based on the time for relative tumor volume of each animal to reach 1600% between the control group (group 1) and the cyclophosphamide monotherapy group (group 5).

In order to examine the influence of the combination therapy group of compound A and cyclophosphamide on tumor growth delay, the two-tailed Steel test was performed for the comparison of each monotherapy group (groups 2 and 5) to the combination therapy group (group 6), the comparison of each monotherapy group (groups 3 and 5) to the combination therapy group (group 7), and the comparison of each monotherapy group (groups 4 and 5) to the combination therapy group (group 8), for the time until the relative tumor volume reached 1600%. A combination effect was determined to be present when the combination therapy group was significant relative to each monotherapy group.

As a significant difference was observed in the combination therapy group against each monotherapy group, two-way ANOVA (two-tailed, factors: group and dosage) was performed to evaluate the interaction effect between the compound A-treated groups (groups 1 and 2) and the cyclophosphamide-treated groups (groups 5 and 6), between the compound A-treated groups (groups 1 and 3) and the cyclophosphamide-treated groups (groups 5 and 7), and between the compound A-treated groups (groups 1 and 4) and the cyclophosphamide-treated groups (groups 5 and 8).

7) Results

The time required for the relative tumor volume, which was the evaluation endpoint, to reach 1600% was 12.7 days (median time) in the control group. In the monotherapies, the tumor growth delay rate (%) at 10, 30, and 100 mg/kg of compound A was 3.5%, 81.1%, and 147.6%, respectively. The tumor growth delay rate (%) at 50 mg/kg of cyclophosphamide was 83.9%. It was shown that monotherapy of 30 or 100 mg/kg of compound A or 50 mg/kg of cyclophosphamide was effective.

In the combination therapies, the group of 10 mg/kg of compound A+50 mg/kg of cyclophosphamide, the group of 30 mg/kg of compound A+50 mg/kg of cyclophosphamide, and the group of 100 mg/kg of compound A+50 mg/kg of cyclophosphamide showed a tumor growth delay rate (%) of >287.0%, >293.7%, and >293.7%, respectively. When compound A was administered in combination with cyclophosphamide, a combination effect and a significant interaction were observed, and the combination effect was significantly synergistic. In the combination therapy, tumors were reduced at compound A 10 mg/kg and higher and completely regressed at compound A 30 mg/kg and higher. Further, in the administration groups of 30 or 100 mg/kg of compound A in combination with cyclophosphamide, no tumor regrowth was observed during the observation period after administration (Day 16 to Day 51) (Table 3, and FIGS. 36, 37, and 38).

8) Conclusion

These results demonstrate that compound A monotherapy at 30 or 100 mg/kg, cyclophosphamide monotherapy at 50 mg/kg, and the combination therapy of compound A at 10, 30, or 100 mg/kg with cyclophosphamide at 50 mg/kg have an antitumor effect on OCI-Ly7 tumor. The combination therapies were well-tolerated and showed significantly synergistic effects.

TABLE 3

| Group | Median Time (days) | Tumor growth delay (days) | Tumor growth delay rate (%) | P value | P value[c] | p value[d] | P value[e] |
|---|---|---|---|---|---|---|---|
| Control group (solvent control) | 12.7 | 0 | 0 | — | — | — | — |
| Compound A (10 mg/kg) treated group | 13.2 | 0.5 | 3.5 | 0.2197[a] | <0.01 | — | — |
| Compound A (30 mg/kg) treated group | 23.0 | 10.3 | 81.1 | <0.01[a] | — | <0.01 | — |

TABLE 3-continued

| Group | Median Time (days) | Tumor growth delay (days) | Tumor growth delay rate (%) | P value | P value[c] | p value[d] | P value[e] |
|---|---|---|---|---|---|---|---|
| Compound A (100 mg/kg) treated group | 31.5 | 18.8 | 147.6 | <0.01[a] | — | — | <0.01 |
| Cyclophosphamide (50 mg/kg) treated group | 23.4 | 10.7 | 83.9 | <0.01[b] | <0.01 | <0.01 | <0.01 |
| Compound A (10 mg/kg) + cyclophosphamide (50 mg/kg) treated group | >49.2 | >36.5 | >287.0 | — | — | — | — |
| Compound A (30 mg/kg) + cyclophosphamide (50 mg/kg) treated group | >50.0 | >37.3 | >293.7 | — | — | — | — |
| Compound A (100 mg/kg) cyclophosphamide (50 mg/kg) treated group | >50.0 | >37.3 | >293.7 | — | — | — | — |

[a]Steel test results of the control group and each compound A monotherapy group for the evaluation endpoint (relative tumor volume 1600%)
[b]Wilcoxcon rank sum test results of the control group and the cyclophosphamide monotherapy group for the evaluation endpoint (relative tumor volume 1600%)
[c,d,e]Steel test results each monotherapy group (10 mg/kg, 30 mg/kg, or 100 mg/kg of compound A, or 50 mg/kg of cyclophosphamide) and the corresponding combination therapy groups (compound A + 50 mg/kg of cyclophosphamide) for the evaluation endpoint (relative tumor volume 1600%)
Since a significant difference in tumor growth delay was observed between the combination therapy groups and the corresponding monotherapy groups (50 mg/kg of cyclophosphamide and each dose of compound A), two-way ANOVA was performed to evaluate the interaction effect by comparison between non-cyclophosphamide-treated groups (control, compound A monotherapy) and cyclophosphamide-treated groups (cyclophosphamide monotherapy, combination therapy). A significant synergetic effect was observed in the interaction effect of the combination therapy groups (p < 0.01).

Example 37: Combination Effect of Compound A and Lapatinib on Human Breast Cancer Cell Line MDA-MB-453

1) Test Substance

The compound A bulk powder was used. Lapatinib used was Lapatinib, Di-p-Toluenesulfonate Salt, purchased from LC Laboratories.

2) Preparation of Test Substance

Compound A was suspended in a 1% hypromellose solution to prepare 20 mg/mL test substance suspensions (a suspension for preparing a single administration solution and a suspension for preparing a 100 mg/kg combined administration solution). The 20 mg/mL test substance suspensions were diluted with a 1% hypromellose solution to prepare 10 mg/mL (100 mg/kg administration solution), 6 mg/mL (suspension for preparing a 30 mg/kg combined administration solution), and 3 mg/mL (30 mg/kg administration solution) test substance suspensions. Lapatinib was suspended in a 1% hypromellose solution to prepare a 20 mg/mL suspension for preparing a 100 mg/kg lapatinib combined administration solution. The 20 mg/mL suspension was diluted with a 1% hypromellose solution to prepare a 10 mg/mL suspension for 100 mg/kg single administration. The administration solution of the combination group was prepared by mixing the 6 mg/mL compound A suspension and the 20 mg/mL lapatinib suspension at 1:1, or mixing the 20 mg/mL compound A suspension and the 20 mg/mL lapatinib suspension at 1:1.

3) Cells

MDA-MB-453 was obtained from ATCC. The cells were cultured in RPMI 1640 medium supplemented with 10% inactivated (treated at 56° C. for 30 minutes) fetal bovine serum under the conditions of 37° C. and 5% $CO_2$. The collected cells were suspended in serum-free RPMI 1640 medium at $1.0 \times 10^8$ cells/mL.

4) Animal 5-week-old female NOD-SCID mice (NOD.CB17-Prkdcscid/J, produced by Charles River Japan Co., Ltd.) were used. The female NOD-SCID mice were bred in the same manner as in Example 36. The cell suspension was inoculated at $2 \times 10^7$ cells/body into the subcutaneous space of the right axillary region of the 6-week-old NOD-SCID mice, and the mice were grouped in the same manner as in Example 36 using the tumor volume as an index.

5) Administration and Measurement

The administration was started on the next day of the grouping (Day 2), and compound A and lapatinib were orally administered once a day for 28 consecutive days. Each group (N=8) was treated as follows.

(1) Control (solvent control) group: 1% hypromellose solution
(2) Compound A (30 mg/kg) treated group: 30 mg/kg of compound A (oral administration once a day for 28 consecutive days)
(3) Compound A (100 mg/kg) treated group: 100 mg/kg of compound A (oral administration once a day for 28 consecutive days)
(4) Lapatinib (100 mg/kg) treated group: 100 mg/kg of lapatinib (oral administration once a day for 28 consecutive days)
(5) Combination group 1: 30 mg/kg of compound A (oral administration once a day for 28 consecutive days)+ 100 mg/kg of lapatinib (oral administration once a day for 28 consecutive days)
(6) Combination group 2: 100 mg/kg of compound A (oral administration once a day for 28 consecutive days)+ 100 mg/kg of lapatinib (oral administration once a day for 28 consecutive days)

The measurement, calculation of tumor growth delay, and statistical analysis were performed in the same manner as in Example 36.

6) Results

The time required for the relative tumor volume, which was the evaluation endpoint, to reach 200% was 22.8 days (median time) in the control group. In the monotherapies, the tumor growth delay rate (%) at 30 and 100 mg/kg of compound A was 72.4% and >334.2%, respectively. The tumor growth delay rate (%) at 100 mg/kg of lapatinib was 50.0%. It was shown that the monotherapy of 30 or 100 mg/kg of compound A or 100 mg/kg of lapatinib was effective.

In the combination therapies, the group of 30 mg/kg of compound A+100 mg/kg of lapatinib, and the group of 100 mg/kg of compound A+100 mg/kg of lapatinib both showed a tumor growth delay rate (%) of >334.2%. When 30 mg/kg of compound A was administered in combination with 100 mg/kg of lapatinib, a combination effect and a significant interaction were observed, and the combination effect was significantly synergistic. In the combination therapy, the tumor completely regressed at both doses of compound A. Further, in the group of 100 mg/kg of compound A+100 mg/kg of lapatinib, no tumor regrowth was observed until 2 months after the completion of the combined administration (Table 4, and FIGS. 39 and 40).

7) Conclusion

These results demonstrate that compound A monotherapy at 30 or 100 mg/kg, lapatinib monotherapy at 100 mg/kg, and the combination therapy of compound A at 30 or 100 mg/kg with lapatinib at 100 mg/kg all have antitumor effects on MDA-MB-453 tumors. The combination therapies were well-tolerated and showed significantly synergistic effects.

3) Cells

OCI-Ly7 was obtained from DSMZ. The cells were cultured in RPMI 1640 medium supplemented with 10% inactivated (treated at 56° C. for 30 minutes) fetal bovine serum under the conditions of 37° C. and 5% $CO_2$. The collected cells were suspended in serum-free RPMI 1640 medium at $1.5 \times 10^8$ cells/mL.

4) Animal 5-week-old female SCID mice (C.B-17/Icr-scid/scid Jcl, produced by CLEA Japan, Inc.) were used. The female SCID mice were bred in the same manner as in Example 36. The cell suspension was inoculated at $3 \times 10^7$ cells/body into the subcutaneous space of the right axillary region of the 6-week-old SCID mice, and the mice were grouped in the same manner as in Example 36 using the tumor volume as an index.

5) Administration and Measurement

The administration was started on the next day of the grouping (Day 2). Compound A was orally administered once a day for 14 consecutive days, and bendamustine was administered intraperitoneally on Days 2, 3, 4, 5, and 6, 5 times in total. In order to match with the combination group, a solvent of each drug was administered to the control group, and a solvent of the combined drug was administered to the

TABLE 4

| Group | Median Time (days) | Tumor growth delay (days) | Tumor growth delay rate (%) | P value | P value[c] | P value[d] |
|---|---|---|---|---|---|---|
| Control group (solvent control) | 22.8 | 0 | 0 | — | — | — |
| Compound A (30 mg/kg) treated group | 39.3 | 16.5 | 72.4 | <0.01[a] | <0.01 | — |
| Compound A (100 mg/kg) treated group | >99.0 | >76.2 | >334.2 | <0.01[a] | — | 0.2456 |
| Lapatinib (100 mg/kg) treated group | 34.2 | 11.4 | 50.0 | <0.01[b] | <0.01 | <0.01 |
| Compound A (30 mg/kg) + lapatinib (100 mg/kg) treated group | >99.0 | >76.2 | >334.2 | — | — | — |
| Compound A (100 mg/kg) + lapatinib (100 mg/kg) treated group | >99.0 | >76.2 | >334.2 | — | — | — |

[a]Steel test results of the control group and each compound A monotherapy group for the evaluation endpoint (relative tumor volume 200%)
[b]Wilcoxcon rank sum test results of the control group and the lapatinib monotherapy group for the evaluation endpoint (relative tumor volume 200%)
[c,d]Steel test results each monotherapy group (30 mg/kg or 100 mg/kg of compound A or 100 mg/kg of lapatinib) and corresponding combination therapy groups (compound A + 100 mg/kg of lapatinib) for the evaluation endpoint (relative tumor volume 200%)
Since a significant difference in tumor growth delay was observed between the combination therapy group of 30 mg/kg of compound A + 100 mg/kg of lapatinib and the corresponding monotherapy groups, two-way ANOVA was performed to evaluate the interaction effect by comparison between non-lapatinib-treated groups (control, compound A monotherapy) and lapatinib-treated groups (lapatinib monotherapy, combination therapy). A significant synergetic effect was observed in the interaction effect of the combination therapy groups ($p < 0.01$).

Example 38: Combination Effect of Compound A and Bendamustine on Human Diffuse Large B-Cell Lymphoma Cell Line OCI-Ly7

1) Test Substance

The compound A bulk powder was used. Bendamustine used was Bendamustine hydrochloride hydrate, purchased from Tokyo Chemical Industry Co., Ltd.

2) Preparation of Test Substance

Compound A was suspended in a 1% hypromellose solution to prepare a 3 mg/mL (30 mg/kg administration solution) test substance suspension. Bendamustine was dissolved in saline, and a 1.5 mg/mL solution (15 mg/kg administration solution) was prepared at the time of use.

single administration group, as in the combination group. All of the animals received oral administration for 14 consecutive days, and intraperitoneal administration on Days 2, 3, 4, 5, and 6 (5 times in total). Each group (N=6) was treated as follows.

(1) Control (solvent control) group: 1% hypromellose solution, saline (2) Compound A (30 mg/kg) treated group: 30 mg/kg of compound A (oral administration once a day for 14 consecutive days)

(3) Bendamustine (15 mg/kg) treated group: 15 mg/kg of bendamustine (intraperitoneal administration on Days 2, 3, 4, 5, and 6)

(4) Combination group: 30 mg/kg of compound A (oral administration once a day for 14 consecutive days)+15 mg/kg of bendamustine (intraperitoneal administration on Days 2, 3, 4, 5, and 6)

The measurement, calculation of tumor growth delay, and statistical analysis were performed in the same manner as in Example 36.

6) Results

The time required for the relative tumor volume, which was the evaluation endpoint, to reach 1600% was 15.5 days (median time) in the control group. In the monotherapy, the tumor growth delay rate (%) at 30 mg/kg of compound A was 54.2%. The tumor growth delay rate (%) at 15 mg/kg of bendamustine was 56.5%. It was shown that the monotherapy of 30 mg/kg of compound A or 15 mg/kg of bendamustine was effective.

In the combination therapy, the group of 30 mg/kg of compound A+15 mg/kg of bendamustine showed a tumor growth delay rate (%) of >222.6%. When compound A was administered in combination with bendamustine, a combination effect and a significant interaction were observed, and the combination effect was significantly synergistic. Further, the tumor completely regressed by the combination therapy (Table 5 and FIG. 41).

7) Conclusion

These results demonstrate that compound A monotherapy at 30 mg/kg, bendamustine monotherapy at 15 mg/kg, and the combination therapy of compound A at 30 mg/kg with bendamustine at 15 mg/kg have an antitumor effect on OCI-Ly7 tumor. The combination therapy was well-tolerated and showed significantly synergistic effects.

TABLE 5

| Group | Median Time (days) | Tumor growth delay (days) | Tumor growth delay rate (%) | P value[a] | P value[b] |
|---|---|---|---|---|---|
| Control group (solvent control) | 15.5 | 0 | 0 | — | — |
| Compound A (30 mg/kg) treated group | 23.9 | 8.4 | 54.2 | <0.01 | <0.01 |
| Bendamustine (15 mg/kg) treated group | 24.3 | 8.8 | 56.5 | <0.01 | <0.01 |
| Compound A (30 mg/kg) + bendamustine (15 mg/kg) treated group | >50.0 | >34.5 | >222.6 | — | — |

[a]Wilcoxon rank sum test results of the control group and each compound A monotherapy group, and the control group and the bendamustine monotherapy group, for the evaluation endpoint (relative tumor volume 1600%)
[b]Steel test results of each monotherapy group (30 mg/kg of compound A or 15 mg/kg of bendamustine) and the combination therapy group (30 mg/kg of compound A + 15 mg/kg of bendamustine) for the evaluation endpoint (relative tumor volume 1600%)
Since a significant difference in tumor growth delay was observed between the combination therapy group and the corresponding monotherapy groups, two-way ANOVA was performed to evaluate the interaction effect by comparison between non-bendamustine-treated groups (control, compound A monotherapy) and bendamustine-treated groups (bendamustine monotherapy, combination therapy). A significant synergistic effect was observed in the interaction effect of the combination therapy group (p < 0.01).

Example 39: Combination Effect of Compound A and Rituximab on Human Diffuse Large B-Cell Lymphoma Cell Line OCI-Ly7

1) Test Substance

The compound A bulk powder was used. Rituximab (Rituxan (trademark) 100 mg/10 mL) used was purchased from Genentech, Inc.

2) Preparation of Test Substance

Compound A was suspended in a 1% hypromellose solution to prepare a 3 mg/mL (30 mg/kg administration solution) test substance suspension. Rituximab was diluted with saline, and a 1 mg/mL solution (10 mg/kg administration solution) was prepared at the time of use.

3) Cells

OCI-Ly7 was obtained from DSMZ. The cells were cultured in RPMI 1640 medium supplemented with 10% inactivated (treated at 56° C. for 30 minutes) fetal bovine serum under the conditions of 37° C. and 5% $CO_2$. The collected cells were suspended in serum-free RPMI 1640 medium at $1.5 \times 10^8$ cells/mL.

4) Animal 5-week-old female nude mice (BALB/c Slc-nu/nu, produced by Japan SLC, Inc.) were used. The female nude mice were bred in the same manner as in Example 36. The cell suspension was inoculated at $3 \times 10^7$ cells/body into the subcutaneous space of the right axillary region of the 6-week-old nude mice, and the mice were grouped in the same manner as in Example 36 using the tumor volume as an index.

5) Administration and Measurement

The administration was started on the next day of the grouping (Day 2). Compound A was orally administered once a day for 21 consecutive days, and rituximab was administered intraperitoneally on Days 2, 9, and 16, 3 times in total. In order to match with the combination group, a solvent of each drug was administered to the control group, and a solvent of the combined drug was administered to the single administration group, as in the combination group. All of the animals received oral administration for 21 consecutive days, and intraperitoneal administration on Days 2, 9, and 16 (3 times in total). Each group (N=6) was treated as follows.

(1) Control (solvent control) group: 1% hypromellose solution, saline
(2) Compound A (30 mg/kg) treated group: 30 mg/kg of compound A (oral administration once a day for 21 consecutive days)
(3) Rituximab treated group: 10 mg/kg of rituximab (intraperitoneal administration on Days 2, 9, and 16)
(4) Combination group: 30 mg/kg of compound A (oral administration once a day for 21 consecutive days)+10 mg/kg of rituximab (intraperitoneal administration on Days 2, 9, and 16)

The measurement, calculation of tumor growth delay, and statistical analysis were performed in the same manner as in Example 36.

6) Results

The time required for the relative tumor volume, which was the evaluation endpoint, to reach 600% was 16.3 days (median time) in the control group. In the monotherapy, the tumor growth delay rate (%) at 30 mg/kg of compound A was 73.9%. The tumor growth delay rate (%) at 10 mg/kg of rituximab was 74.2%. It was shown that the monotherapy of 30 mg/kg of compound A or 10 mg/kg of rituximab was effective.

In the combination therapy, the group of 30 mg/kg of compound A+10 mg/kg of rituximab showed a tumor growth delay rate (%) of >421.5%. When compound A was administered in combination with rituximab, a combination effect and a significant interaction were observed, and the combination effect was significantly synergistic. Further, the tumor completely regressed by the combination therapy (Table 6 and FIG. 42).

7) Conclusion

These results demonstrate that compound A monotherapy at 30 mg/kg, rituximab monotherapy at 10 mg/kg, and the combination therapy of compound A at 30 mg/kg with rituximab at 10 mg/kg have an antitumor effect on OCI-Ly7 tumor. The combination therapy was well-tolerated and showed significantly synergistic effects.

TABLE 6

| Group | Median Time (days) | Tumor growth delay (days) | Tumor growth delay rate (%) | P value[a] | P value[b] |
|---|---|---|---|---|---|
| Control group (solvent control) | 16.3 | 0 | 0 | — | — |
| Compound A (30 mg/kg) treated group | 28.4 | 12.1 | 73.9 | <0.01 | <0.01 |
| Rituximab (10 mg/kg) treated group | 28.4 | 12.1 | 74.2 | <0.01 | <0.01 |
| Compound A (30 mg/kg) + rituximab (10 mg/kg) treated group | >85.0 | >68.7 | >421.5 | — | — |

[a]Wilcoxon rank sum test results of the control group and each compound A monotherapy group, and the control group and the rituximab monotherapy group, for the evaluation endpoint (relative tumor volume 600%)
[b]Steel test results of each monotherapy group (30 mg/kg of compound A or 10 mg/kg of rituximab) and the combination therapy group (30 mg/kg compound A + 10 mg/kg of rituximab) for the evaluation endpoint (relative tumor volume 600%)
Since a significant difference in tumor growth delay was observed been the combination therapy group and the corresponding monotherapy groups, two-way ANOVA was performed to evaluate the interaction effect by comparison between non-rituximab-treated groups (control, compound A monotherapy) and rituximab-treated groups (rituximab monotherapy, combination therapy). A significant synergistic effect was observed in the interaction effect of the combination therapy group ($p < 0.01$).

Example 40: Combination Effect of Compound A and Decitabine on Human Acute Myelogenous Leukemia (AML) Cell Line KG-1

1) Test Substance

The compound A bulk powder was used. Decitabine (5-aza-2'-deoxycytidine) used was purchased from Tokyo Chemical Industry Co., Ltd.

2) Preparation of Test Substance

Compound A was suspended in a 1% hypromellose solution to prepare a 3 mg/mL administration solution of 30 mg/kg of compound A. Decitabine was diluted with saline to prepare a 0.1 mg/mL administration solution of 1 mg/kg of decitabine.

3) Cells

KG-1 was obtained from the Health Science Research Resources Bank. The cells were cultured in RPMI 1640 medium supplemented with 10% inactivated (treated at 56° C. for 30 minutes) fetal bovine serum under the conditions of 37° C. and 5% $CO_2$. The collected cells were suspended in serum-free RPMI 1640 medium at $2.5 \times 10^8$ cells/mL.

4) Animal 5-week-old female SCID mice (C.B-17/Icr-scid/scid Jcl, produced by CLEA Japan, Inc.) were used. The female SCID mice were bred in the same manner as in Example 36. The cell suspension was inoculated at $5 \times 10^7$ cells/body into the subcutaneous space of the right axillary region of the 6-week-old SCID mice, and the mice were grouped in the same manner as in Example 36 using the tumor volume as an index.

5) Administration and Measurement

The administration was started on the next day of the grouping (Day 2), and the tumor diameter and body weight were finally measured and evaluated on the next day after the completion of the 21-day administration (Day 23). Each group (N=8) was treated as follows. In order to match with the combination group, a solvent of each drug was administered to the control group, and a solvent of the combined drug was administered to the single administration group, as in the combination group.

(1) Control (solvent control) group: 1% hypromellose solution, saline
(2) Compound A-treated group: 30 mg/kg of compound A (oral administration once a day for 21 consecutive days)
(3) Decitabine treated group: 1 mg/kg of decitabine (intraperitoneal administration on Days 2, 5, 9, 12, 16, and 19)
(4) Combination group: 30 mg/kg of compound A (oral administration once a day for 21 consecutive days)+1 mg/kg of decitabine (intraperitoneal administration on Days 2, 5, 9, 12, 16, and 19) The body weight and the tumor diameter were measured over time using an electronic balance and electronic digital caliper.

The tumor volume was calculated from tumor diameters by the following formula: (Long diameter×[Short diameter]$^2 \times 0.5$). The antitumor activity was expressed as the ratio of the relative tumor volume of each treated group to the control group (T/C %). The T/C % on Day 23 was calculated for each group by the formula: relative tumor volume of each group on Day 23 [(tumor volume of each group on Day 23/tumor volume of each group on Day 1)×100]/average relative tumor volume of control group on Day 23 [(tumor volume of control group on Day 23/tumor volume of control group on Day 1)×100]×100.

6) Statistical Analysis

The influence of the combination of compound A and decitabine (group 4) on relative tumor volume (Day 23) was evaluated by Dunnett test (two-tailed) against compound A alone (group 2) and decitabine alone (group 3). As a significant difference was observed in group 4 against each monotherapy group, two-way ANOVA (two-tailed) was performed to evaluate the interaction effect between compound A-treated groups (groups 1 and 2) and decitabine-treated groups (groups 3 and 4).

7) Results

Compound A and decitabine showed an antitumor effect on KG-1 tumor. The combination therapy of decitabine and compound A significantly suppressed tumor growth more potently than the monotherapy of each drug (Table 7 and FIG. 43).

8) Conclusion

The combination therapy with compound A and decitabine was well-tolerated and showed significantly synergistic effects in the KG-1 tumor-bearing mouse model. This result supports to conduct clinical trials of the combination chemotherapy with compound A and decitabine.

Example 41: Combination Effect of Compound A and Cytarabine on Human Acute Myelogenous Leukemia (AML) Cell Line KG-1

1) Test Substance

The compound A bulk powder was used. Cytarabine (Cylocide (trademark) Injection, 60 mg) used was purchased from Nippon Shinyaku Co., Ltd.

2) Preparation of Test Substance

Compound A was suspended in a 1% hypromellose solution to prepare a 3 mg/mL administration solution of 30 mg/kg of compound A. Cytarabine was diluted with saline to prepare a 5 mg/mL administration solution of 50 mg/kg of cytarabine.

3) Cells

KG-1 was obtained from the Health Science Research Resources Bank. The cells were cultured in RPMI 1640 medium supplemented with 10% inactivated (treated at 56° C. for 30 minutes) fetal bovine serum under the conditions of 37° C. and 5% $CO_2$. The collected cells were suspended in serum-free RPMI 1640 medium at $2.5 \times 10^8$ cells/mL.

4) Animal 5-week-old female SCID mice (C.B-17/Icr-scid/scid Jcl, produced by CLEA Japan, Inc.) were used. The female SCID mice were bred in the same manner as in Example 36. The cell suspension was inoculated at $5 \times 10^7$ cells/body into the subcutaneous space of the right axillary region of the 6-week-old SCID mice, and the mice were grouped in the same manner as in Example 36 using the tumor volume as an index.

5) Administration and Measurement

The administration was started on the next day of the grouping (Day 2). The tumor diameter and body weight were finally measured and evaluated on the next day after the completion of the 14-day administration (Day 16). Each group (N=6) was treated as follows. In order to match with the combination group, a solvent of each drug was administered to the control group, and a solvent of the combined drug was administered to the single administration group, as in the combination group.

(1) Control (solvent control) group: 1% hypromellose solution, saline
(2) Compound A-treated group: 30 mg/kg of compound A (oral administration once a day for 14 consecutive days)
(3) Cytarabine treated group: 50 mg/kg of cytarabine (intraperitoneal administration on Days 2, 3, 4, 5, 6, 9, 10, 11, 12, and 13)
(4) Combination group: 30 mg/kg of compound A (oral administration once a day for 14 consecutive days)+50 mg/kg of cytarabine (intraperitoneal administration on Days 2, 3, 4, 5, 6, 9, 10, 11, 12, and 13)

The body weight and the tumor diameter were measured over time using an electronic balance and electronic digital caliper. The tumor volume was calculated from tumor diameters by the following formula: (Long diameter×[Short diameter]$^2$×0.5). The antitumor activity was expressed as the ratio of the relative tumor volume of each treated group to the control group (T/C %). The T/C % on Day 16 was calculated for each group from the formula: relative tumor volume of each group on Day 16 [(tumor volume of each group on Day 16/tumor volume of each group on Day 1)×100]/average relative tumor volume of control group on Day 16 [(tumor volume of control group on Day 16/tumor volume of control group on Day 1)×100]×100.

6) Statistical Analysis

The influence of the combination of compound A and cytarabine (group 4) on relative tumor volume (Day 16) was evaluated by Dunnett test (two-tailed) against compound A alone (group 2) and cytarabine alone (group 3). As a significant difference was observed in group 4 against each monotherapy group, two-way ANOVA (two-tailed) was performed to evaluate the interaction effect between compound A-treated groups (groups 1 and 2) and cytarabine-treated groups (groups 3 and 4).

7) Results

Compound A and cytarabine showed an antitumor effect on KG-1 tumor. The combination therapy of cytarabine and compound A significantly suppressed tumor growth more potently than the monotherapy of each drug (Table 7 and FIG. 44).

8) Conclusion

The combination therapy with compound A and cytarabine was well-tolerated and showed significantly synergistic effects in the KG-1 tumor-bearing mouse model. This result supports to conduct clinical trials of the combination chemotherapy with compound A and cytarabine.

TABLE 7

| | | Compound A monotherapy (orally, daily, administration) | | Monotherapy of other antitumor active substance Combined drug (dose [mg/kg], administration route, | | Combination therapy |
|---|---|---|---|---|---|---|
| Origin | Cell line | Dose [mg/kg] | T/C (%) | administration frequency) | T/C (%) | T/C (%) |
| Acute myelogenous leukemia | KG-1 | 30 | 45.2 | Decitabine (1, intraperitoneally, twice a week) | 27.7 | 5.2* |
| Acute myelogenous leukemia | KG-1 | 30 | 52.0 | Cytarabine (50, intraperitoneally, 5-day administration and 2-day cessation) | 62.3 | 5.4* |

*Synergistic combination effect

Example 42: Three-Drug Combination Effect of Compound A, Bendamustine, and Rituximab on Human Diffuse Large B-Cell Lymphoma Cell Line OCI-Ly7

1) Test Substance

The compound A bulk powder was used. Bendamustine used was Bendamustine hydrochloride hydrate, purchased from Tokyo Chemical Industry Co., Ltd. Rituximab (Rituxan (trademark) 100 mg/10 mL) used was purchased from Genentech, Inc.

2) Preparation of Test Substance

Compound A was suspended in a 1% hypromellose solution to prepare a 3 mg/mL (30 mg/kg administration solution) test substance suspension. Bendamustine was dissolved in saline, and a 1 mg/mL solution (10 mg/kg administration solution) was prepared at the time of use. Rituximab was diluted with saline, and a 1 mg/mL solution (10 mg/kg administration solution) was prepared at the time of use.

3) Cells

OCI-Ly7 was obtained from DSMZ. The cells were cultured in RPMI 1640 medium supplemented with 10% inactivated (treated at 56° C. for 30 minutes) fetal bovine serum under the conditions of 37° C. and 5% $CO^2$. The collected cells were suspended in serum-free RPMI 1640 medium at $1.5 \times 10^8$ cells/mL.

4) Animal 5-week-old female SCID mice (C.B-17/Icr-scid/scid Jcl, produced by CLEA Japan, Inc.) were used. The female SCID mice were bred in the same manner as in Example 36. The cell suspension was inoculated at $3 \times 10^7$ cells/body into the subcutaneous space of the right axillary region of the 6-week-old SCID mice, and the mice were grouped in the same manner as in Example 36 using the tumor volume as an index.

5) Administration and Measurement

The administration was started on the next day of the grouping (Day 2). Compound A was orally administered once a day for 14 consecutive days. Bendamustine was administered intraperitoneally on Days 2, 3, 4, 5, and 6, 5 times in total. Rituximab was administered intraperitoneally on Days 2 and 9, twice in total. In order to match with the combination group, a solvent of each drug was administered to the control group, and a solvent of the combined drug was administered to the single administration group, as in the combination group. All of the animals received oral administration for 14 consecutive days, and intraperitoneal administration on Days 2, 3, 4, 5, 6, and 9. Each group (N=6) was treated as follows.

(1) Control (solvent control) group: 1% hypromellose solution, saline (2) Compound A (30 mg/kg) treated group: 30 mg/kg of compound A (oral administration once a day for 14 consecutive days)

(3) Bendamustine (10 mg/kg)+rituximab (10 mg/kg) treated group: 10 mg/kg of bendamustine (intraperitoneal administration on Days 2, 3, 4, 5, and 6)+10 mg/kg of rituximab (intraperitoneal administration on Days 2 and 9)

(4) Three-drug combination group: 30 mg/kg of compound A (oral administration once a day for 14 consecutive days)+10 mg/kg of bendamustine (intraperitoneal administration on Days 2, 3, 4, 5, and 6)+10 mg/kg of rituximab (intraperitoneal administration on Days 2 and 9)

The measurement, calculation of tumor growth delay, and statistical analysis were performed in the same manner as in Example 36.

6) Results

The time required for the relative tumor volume, which was the evaluation endpoint, to reach 800% was 9.9 days (median time) in the control group. The compound A (30 mg/kg) treated group showed a tumor growth delay rate (%) of 83.8%. The bendamustine (10 mg/kg)+rituximab (10 mg/kg) treated group showed a tumor growth delay rate (%) of 144.4%. It was shown that 30 mg/kg of compound A and 10 mg/kg of bendamustine+10 mg/kg of rituximab were effective.

In the three-drug combination therapy, the administration group of 30 mg/kg of compound A+10 mg/kg of bendamustine+10 mg/kg of rituximab showed a tumor growth delay rate (%) of >829.3%. When compound A was administered in combination with bendamustine and rituximab, a three-drug combination effect and a significant interaction were observed, and the three-drug combination effect was significantly synergistic. Further, the tumor completely regressed by the three-drug combination therapy (Table 8 and FIG. 45).

7) Conclusion

It was shown that the monotherapy of 30 mg/kg of compound A, the combined therapy of 10 mg/kg of bendamustine+10 mg/kg of rituximab, and the three-drug combined therapy of 30 mg/kg of compound A, 10 mg/kg of bendamustine, and 10 mg/kg of rituximab had significant antitumor activity in the OCI-Ly7 tumor-bearing mouse model. The three-drug combination therapy was well-tolerated and showed significantly synergistic effects.

TABLE 8

| Group | Median Time (days) | Tumor growth delay (days) | Tumor growth delay rate (%) | P value[a] | P value[b] |
|---|---|---|---|---|---|
| Control gap (solvent control) | 9.9 | 0 | 0 | — | — |
| Compound A (30 mg/kg) treated group | 18.2 | 8.3 | 83.8 | <0.01 | <0.01 |
| Bendamustine (10 mg/kg) + rituximab (10 mg/kg) treated group | 24.2 | 14.3 | 144.4 | <0.01 | <0.01 |
| Compound A (30 mg/kg) + bendamustine (10 mg/kg) + rituximab (10 mg/kg) treated group | >92.0 | >82.1 | >829.3 | — | — |

[a]Wilcoxon rank sum test results of the control group and the compound A-treated group, and the control group and the bendamustine + rituximab treated group for the evaluation endpoint (relative tumor volume 800%)
[b]Steel test results of the compound A (30 mg/kg) treated group, bendamustine (10 mg/kg) + rituximab (10 mg/kg) treated group, and the three-drug treated group (30 mg/kg of compound A 10 mg/kg of bendamustine + 10 mg/kg of rituximab ) for the evaluation endpoint (relative tumor volume 800%)
Since a signficant difference in tumor growth delay was observed between the three-drug treated group, the corresponding compound A (30 mg/kg) treated group, and the bendamustine (10 mg/kg) + rituximab (10 mg/kg) treated group, two-way ANOVA was performed to evaluate the interaction effect by comparison between non-bendamustine + rituximab treated grows (control, compound A-treated group) and bendamustine + rituximab treated groups (bendamustine + rituximab treated group, three-drug treated group). A significant synergistic effect was observed in the interaction effect of the three-drug heated group (p < 0.01).

Example 43: Three-Drug Combination Effect of Compound A, Decitabine, and Venetoclax on Human Acute Myelogenous Leukemia (AML) Cell Line KG-1

1) Test Substance

The compound A bulk powder was used. Venetoclax used was purchased from LC Laboratories. Decitabine (5-aza-2'-deoxycytidine) used was purchased from Tokyo Chemical Industry Co., Ltd.

2) Preparation of Test Substance

Compound A and venetoclax were suspended in a 1% hypromellose solution to prepare a 5 mg/mL administration solution of 50 mg/kg of compound A. Decitabine was diluted with saline to prepare a 0.1 mg/mL administration solution of 1 mg/kg of decitabine.

3) Cells

KG-1 was obtained from the Health Science Research Resources Bank. The cells were cultured in RPMI 1640 medium supplemented with 10% inactivated (treated at 56° C. for 30 minutes) fetal bovine serum under the conditions of 37° C. and 5% $CO^2$. The collected cells were suspended in serum-free RPMI 1640 medium at $2.5 \times 10^8$ cells/mL.

4) Animal 5-week-old female SCID mice (C.B-17/Icr-scid/scid Jcl, produced by CLEA Japan, Inc.) were used. The female SCID mice were bred in the same manner as in Example 36. The cell suspension was inoculated at $5 \times 10^7$ cells/body into the subcutaneous space of the right axillary region of the 6-week-old SCID mice, and the mice were grouped in the same manner as in Example 36 using the tumor volume as an index.

5) Administration and Measurement

The administration was started on the next day of the grouping (Day 2), and the tumor diameter and body weight were finally measured and evaluated on the next day after the completion of the 14-day administration (Day 16). Each group (N=6) was treated as follows. In order to match with the combination group, a solvent of each drug was administered to the control group, and a solvent of the combined drug was administered to the single administration group, as in the combination group.

(1) Control (solvent control) group: 1% hypromellose solution, saline
(2) Compound A-treated group: 50 mg/kg of compound A (oral administration once a day for 14 consecutive days)
(3) Venetoclax+decitabine treated group: 50 mg/kg of venetoclax (oral administration once a day for 14 consecutive days)+1 mg/kg of decitabine (intraperitoneal administration on Days 2, 5, 9, and 12)
(4) Three-drug combination group: 50 mg/kg of compound A (oral administration once a day for 14 consecutive days)+50 mg/kg of venetoclax (oral administration once a day for 14 consecutive days)+1 mg/kg of decitabine (intraperitoneal administration on Days 2, 5, 9, and 12)

The body weight and the tumor diameter were measured over time using an electronic balance and electronic digital caliper. The tumor volume was calculated from tumor diameters by the following formula: (Long diameter×[Short diameter]$^2$×0.5). The antitumor activity was expressed as the ratio of the relative tumor volume of each treated group to the control group (T/C %). The T/C % on Day 16 was calculated for each group by the formula: relative tumor volume of each group on Day 16 [(tumor volume of each group on Day 16/tumor volume of each group on Day 1)×100]/average relative tumor volume of control group on Day 16 [(tumor volume of control group on Day 16/tumor volume of control group on Day 1)×100]×100.

6) Statistical Analysis

The influence of the three-drug combination of compound A and venetoclax and decitabine (group 4) on relative tumor volume (Day 16) was evaluated by Dunnett test (two-tailed) against compound A alone (group 2) and venetoclax+decitabine (group 3). As a significant difference was observed in group 4 against group 2 and 3, two-way ANOVA (two-tailed) was performed to evaluate the interaction effect between control and compound A-treated groups (groups 1 and 2) and venetoclax+decitabine-treated group and three-drug combination group (groups 3 and 4).

6) Results

Compound A and venetoclax+decitabine showed an antitumor effect on KG-1 tumor. The three-drug combination therapy of venetoclax, decitabine, and compound A significantly suppressed tumor growth more potently than the single administration of compound A and the administration of venetoclax and decitabine (Table 9 and FIG. 46).

7) Conclusion

The three-drug combination therapy with compound A, venetoclax, and decitabine was well-tolerated and showed significantly synergistic effects in the KG-1 tumor-bearing mouse model. This result supports to conduct clinical trials of the combination chemotherapy with compound A, venetoclax, and decitabine.

TABLE 9

| Origin | Compound A single administraton (oraly, daily administration) | | Other antitumor active substance (II) Combined drug (dose [mg/kg], administration route, | | Combined administration |
|---|---|---|---|---|---|
| | Cell line | Dose [mg/kg] | T/C (%) | administration frequency) | T/C (%) | T/C (%) |
| Acute myelogenous leukemia | KG-1 | 50 | 29.2 | Venetoclax (50, oraly, daily administration) + decitabine (1, intraperitoneally, twice a week) | 32.6 | 1.6* |

*Synergistic combination effect

The invention claimed is:
1. An antitumor composition comprising:
synergistic amounts of the following antitumor agent (A), and
the following compound (B) or a salt thereof:
(A) at least one antitumor agent selected from the group consisting of bendamustine, decitabine, busulfan, lomustine, thiotepa, melphalan, cytarabine, venetoclax, ranimustine, ibrutinib, erlotinib, gefitinib, imatinib, axitinib, lapatinib, lenvatinib, afatinib, gilteritinib, 5-fluorouracil, cyclophosphamide, and rituximab;
(B) a compound or a salt thereof having the following formula (1):

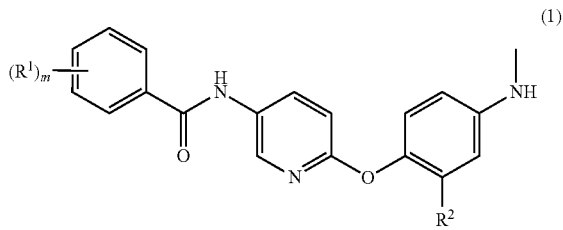

wherein
$R^1$ is a halogen atom or a C1-6 alkyl group, the C1-6 alkyl group being optionally substituted with one or more halogen atoms;
$R^2$ is a hydrogen atom or a C1-6 alkyl group; and
m is an integer of 1 to 2, provided that when m is 2, $R^1$ is the same or different.
2. The composition according to claim 1, wherein compound (B) or a salt thereof is at least one compound or a salt thereof selected from the group consisting of:
N-{6-[2-methyl-4-(methylamino)phenoxy]pyridin-3-yl}-4-(trifluromethyl)benzamide,
2-fluoro-N-{6-[2-methyl-4-(methylamino)phenoxy]pyridin-3-yl}-4-(trifluoromethyl)benzamide,
N-{6-[4-(methylamino)phenoxy]pyridin-3-yl}-4-(trifluoromethyl) benzamide, and
2-fluoro-N-{6-[4-(methylamino)phenoxy]pyridin-3-yl}-4-(trifluoromethyl)benzamide.
3. A kit comprising:
synergistic amounts of the following antitumor agent (A), and
an antitumor composition comprising the following compound (B) or a salt thereof:

(A) at least one antitumor agent selected from the group consisting of bendamustine, decitabine, busulfan, lomustine, thiotepa, melphalan, cytarabine, venetoclax, ranimustine, ibrutinib, erlotinib, gefitinib, imatinib, axitinib, lapatinib, lenvatinib, afatinib, gilteritinib, 5-fluorouracil, cyclophosphamide, and rituximab;

(B) a compound or a salt thereof having the following formula (1):

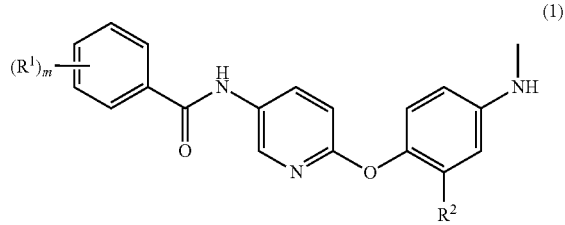

(1)

wherein $R^1$ is a halogen atom or a C1-6 alkyl group, the C1-6 alkyl group being optionally substituted with one or more halogen atoms;

$R^2$ is a hydrogen atom or a C1-6 alkyl group; and m is an integer of 1 to 2, provided that when m is 2, $R^1$ is the same or different.

4. A method for treating a tumor, the method comprising administering synergistic amounts of the following antitumor agent (A) and the following compound (B) or a salt thereof to a subject in need thereof:

(A) at least one antitumor agent selected from the group consisting of bendamustine, decitabine, busulfan, lomustine, thiotepa, melphalan, cytarabine, venetoclax, ranimustine, ibrutinib, erlotinib, gefitinib, imatinib, axitinib, lapatinib, lenvatinib, afatinib, gilteritinib, 5-fluorouracil, cyclophosphamide, and rituximab;

(B) a compound or a salt thereof having the following formula (1):

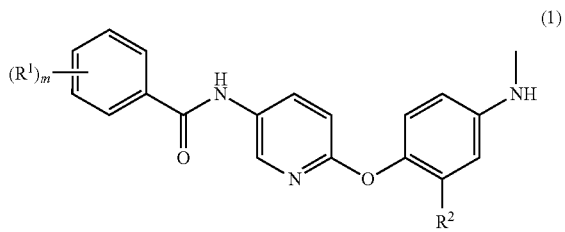

(1)

wherein $R^1$ is a halogen atom or a C1-6 alkyl group, the C1-6 alkyl group being optionally substituted with one or more halogen atoms;

$R^2$ is a hydrogen atom or a C1-6 alkyl group; and m is an integer of 1 to 2, provided that when m is 2, $R^1$ is the same or different.

5. The kit according to claim 3, wherein compound (B) or a salt thereof is at least one compound or a salt thereof selected from the group consisting of: N-{6-[2-methyl-4-(methylamino) phenoxy]pyridin-3-yl}-4-(trifluoromethyl) benzamide, 2-fluoro-N-{6-[2-methyl-4-(methylamino) phenoxy]pyridin-3-yl}-4-(trifluoromethyl) benzamide, N-{6-[4-(methylamino) phenoxy]pyridin-3-yl}-4-(trifluoromethyl) benzamide, and 2-fluoro-N-{6-[4-(methylamino) phenoxy]pyridin-3-yl}-4-(trifluoromethyl) benzamide.

6. The method according to claim 4, wherein compound (B) or a salt thereof is at least one compound or a salt thereof selected from the group consisting of: N-{6-[2-methyl-4-(methylamino) phenoxy]pyridin-3-yl}-4-(trifluoromethyl) benzamide, 2-fluoro-N-{6-[2-methyl-4-(methylamino) phenoxy]pyridin-3-yl}-4-(trifluoromethyl) benzamide, N-{6-[4-(methylamino) phenoxy]pyridin-3-yl}-4-(trifluoromethyl) benzamide, and 2-fluoro-N-{6-[4-(methylamino) phenoxy]pyridin-3-yl}-4-(trifluoromethyl) benzamide.

7. The method according to claim 4, one of the antitumor agent (A) and the compound (B) or a salt thereof is administered several minutes to several tens of minutes or 1 to 12 hours after the completion of the administration of the other.

* * * * *

UNITED STATES PATENT AND TRADEMARK OFFICE
CERTIFICATE OF CORRECTION

PATENT NO. : 12,220,410 B2
APPLICATION NO. : 17/429531
DATED : February 11, 2025
INVENTOR(S) : Naoto Ohi, Mitsuhiro Okuno and Hideo Tanaka Page 1 of 1

It is certified that error appears in the above-identified patent and that said Letters Patent is hereby corrected as shown below:

In the Claims

Column 46, Line 15; In Claim 4, after "wherein", insert --¶--
Column 46, Line 23; In Claim 5, after "of:", insert --¶--
Column 46, Line 25; In Claim 5, after "benzamide,", insert --¶--
Column 46, Line 26; In Claim 5, after "benzamide,", insert --¶--
Column 46, Line 32; In Claim 6, after "of:", insert --¶--
Column 46, Line 34; In Claim 6, after "benzamide,", insert --¶--
Column 46, Line 35; In Claim 6, after "benzamide,", insert --¶--

Signed and Sealed this
Fifteenth Day of April, 2025

Coke Morgan Stewart
*Acting Director of the United States Patent and Trademark Office*